(12) United States Patent
Saadi et al.

(10) Patent No.: US 9,234,006 B2
(45) Date of Patent: Jan. 12, 2016

(54) COMPOUNDS

(71) Applicants: Novacta Biosystems Limited, Hertfordshire (GB); Cantab Anti-Infectives Limited, Berkshire (GB)

(72) Inventors: Mona Saadi, Hertfordshire (GB); Esther Duperchy, Hertfordshire (GB); Pamela Brown, Hertfordshire (GB); Michael John Dawson, Hertfordshire (GB); Sjoerd Nicolaas Wadman, Rheinfelden (DE)

(73) Assignees: Novacta Biosystems Limited, Hertfordshire (GB); Cantab Anti-Infectives Limited, Berkshire (GB)

( * ) Notice: Subject to any disclaimer, the term of this patent is extended or adjusted under 35 U.S.C. 154(b) by 0 days.

(21) Appl. No.: 14/356,868

(22) PCT Filed: Nov. 16, 2012

(86) PCT No.: PCT/GB2012/052844
§ 371 (c)(1),
(2) Date: May 7, 2014

(87) PCT Pub. No.: WO2013/072695
PCT Pub. Date: May 23, 2013

(65) Prior Publication Data
US 2015/0031602 A1   Jan. 29, 2015

Related U.S. Application Data

(60) Provisional application No. 61/561,361, filed on Nov. 18, 2011.

(51) Int. Cl.
| | | |
|---|---|---|
| A01N 37/18 | (2006.01) |
| A61K 38/04 | (2006.01) |
| C07K 7/62 | (2006.01) |
| A61K 38/00 | (2006.01) |

(52) U.S. Cl.
CPC .. *C07K 7/62* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,565,423 | A | 10/1996 | Sandow |
| 5,767,068 | A | 6/1998 | VanDevanter et al. |
| 8,343,912 | B2 | 1/2013 | Leese |
| 8,415,307 | B1 | 4/2013 | Curran et al. |
| 2001/0021697 | A1 | 9/2001 | Lowenstein et al. |
| 2008/0207874 | A1 | 8/2008 | Leese et al. |
| 2008/0279820 | A1 | 11/2008 | Hicks et al. |
| 2009/0215677 | A1 | 8/2009 | Vaara et al. |
| 2009/0239792 | A1 | 9/2009 | Vaara et al. |
| 2010/0160215 | A1 | 6/2010 | Leese |

FOREIGN PATENT DOCUMENTS

| | | |
|---|---|---|
| CN | 101851270 | 10/2010 |
| EP | 571921 | 12/1993 |
| GB | 2128617 | 5/1984 |
| WO | 88/00950 | 2/1988 |
| WO | 2008/017734 | 2/2008 |

(Continued)

OTHER PUBLICATIONS

Tsubery et al. N-terminal modifications of Polymyxin B nonapeptide and their effect on antibacterial activity. Peptides 2001. vol. 22, pp. 1675-1681.*
Bergen et al., "Pharmacokinetics and pharmacodynamics of 'old' polymyxins: what is new?" Diagnostic Microbiology and Infectious Disease, 74: 213-223 (2012).
International Search Report and Written Opinion issued in International Patent Application No. PCT/GB2014/051547 dated Dec. 8, 2014.
Kanazawa et al., "Contribution of Each Amino Acid Residue in Polymyxin B3 to Antimicrobial and Lipopolysaccharide Binding Activity," Chemical & Pharmaceutical Bulletin, 57: 240-244 (2009).
Search Report issued in Great Britain Patent Application No. 1404301.2 dated Dec. 8, 2014.

(Continued)

*Primary Examiner* — Marcela M Cordero Garcia
(74) *Attorney, Agent, or Firm* — Morgan, Lewis & Bockius LLP

(57) ABSTRACT

Provided are compounds, the use of the said compounds in treatment, for example treatment of microbial infections, particularly by Gram negative bacteria. The compounds are polymyxin-based and are represented by the formula (I):

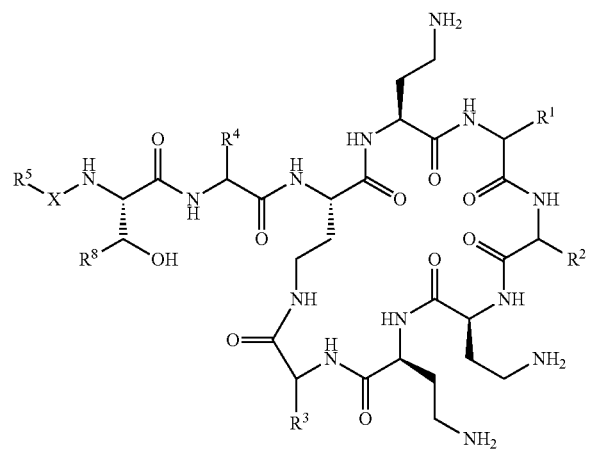

Figure 1:
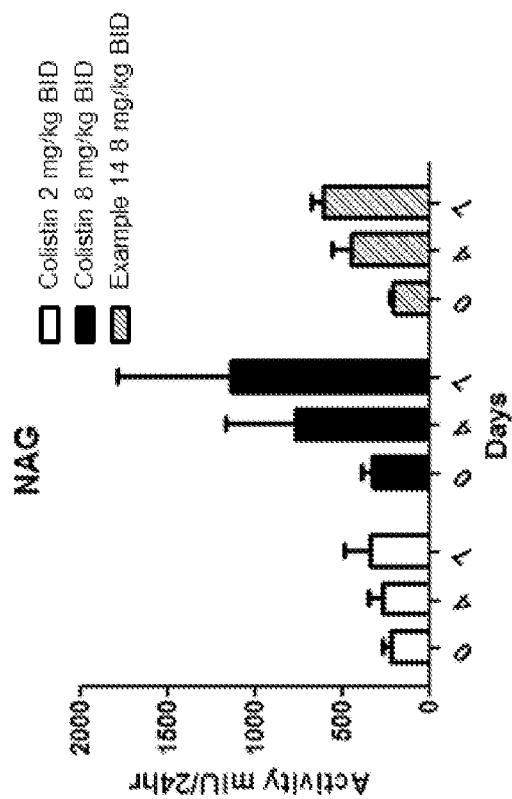
Figure 1:
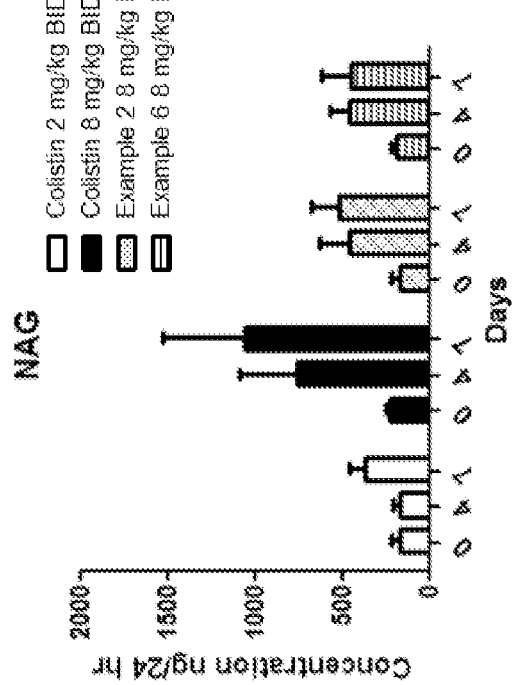

and pharmaceutically acceptable salts thereof, where X is —NHC(O)—, —C(O)—, —OC(O)—, —CH$_2$— or —SO$_2$—; $R^5$ represents $C_{0-12}$ alkyl($C_{4-6}$ heterocyclyl), or $C_{2-12}$ alkyl or $C_{0-12}$ alkyl($C_{3-8}$ cycloalkylyl). and the alkyl or cycloalkylyl bears one, two or three hydroxyl groups, or a —NR$^6$R$^7$ group, or one —NR$^6$R$^7$ group and one or two hydroxyl groups; and R$^1$ to R$^4$ and R$^6$ to R$^8$ are as defined in the description.

26 Claims, 3 Drawing Sheets

(56) References Cited

FOREIGN PATENT DOCUMENTS

| WO | 2009/098357 |    | 8/2009  |
|----|-------------|----|---------|
| WO | 2010/029196 |    | 3/2010  |
| WO | 2010/075416 |    | 7/2010  |
| WO | 2010/130007 | A1 | 11/2010 |
| WO | 2012/051663 | A1 | 4/2012  |
| WO | 2012/168820 |    | 12/2012 |
| WO | 2013/072695 |    | 5/2013  |
| WO | 2014/188178 | A1 | 11/2014 |

OTHER PUBLICATIONS

Sigma-Aldrich, "Chem Files: Peptide Synthesis," 4(2): 1-19 (2007).
Tsubery et al., "Modulation of the Hydrophobic Domain of Polymyxin B Nonapeptide: Effect on Outer-Membrane Permeabilization and Lipopolysaccharide Neutralization," Molecular Pharmacology, 62: 1036-1042 (2002).
Velkov et al., "Teaching 'Old' Polymyxins New Tricks: New-Generation Lipopeptides Targeting Gram-Negative 'Superbugs'," ACS Chemical Biology, 9: 1172-1177 (2014).
Bergen et al., "Colistin methanesulfonate is an inactive prodrug of colistin against Pseudomonas aeruginosa," Antimicrob. Agents and Chemotherapy, 50:1953-1958 (2006).
CAS (Chemical Abstracts Service) Search Results, cited in a search report issued in a related United Kingdom patent application, dated Nov. 20, 2013.
de Visser et al., "Solid-phase synthesis of polymyxin B1 and analogues via a safety-catch approach," J. Peptide Res., 61:298-306 (2003).
Diaz et al., "Fast and efficient access to a family of multifunctional 1,3,5-trisubstituted piperidines," Synthetic Communications, 38:2799-2813 (2008).
Gallou et al., "Practical synthesis of unsymmetrical ureas from isopropenyl carbamates," J. Org. Chem., 70:6960-6963 (2005).
Katsuma et al., "Antimicrobial activity of des-fatty acyl-polymyxin B decapeptide N-terminal analogs," Peptide Science, 41:549-550 (2005).
Katsuma et al., "Development of des-fatty acyl-polymyxin B decapeptide analogs with Pseudomonas aeruginosa-specific antimicrobial activity," Chem. Pharm. Bull., 57:332-336 (2009).
Kimura et al., "Polymyxin B octapeptide and polymyxin B heptapeptide are potent outer membrane permeability-increasing agents," J. Antibiot.(Tokyo), 45:742-749 (1992).
Li et al., "Use of high-performance liquid chromatography to study the pharmacokinetics of colistin sulfate in rats following intravenous administration," Antimicrob. Agents and Chemotherapy, 47:1766-1770 (2003).
Magee et al., "Discovery of Dap-3 polymyxin analogs for the treatment of multidrug-resistant gram-negative nosocomial infections," J. Med. Chem., 56:5079-5093 (2013).
O'Dowd et al., "Preparation of tetra-Boc-protected polymyxin B nonapeptide," Tetrahedron Letters, 48:2003-2005 (2007).
Okimura et al., "Antimicrobial activity of various aminocyclohexylcarbonyl-polymyxin B (2-10) derivatives," Peptide Science, 45:243-244 (2009).
Okimura et al., "Chemical conversion of natural polymyxin B and colistin to their N-terminal derivatives," Bull. Chem. Soc. Japan, 80:543-552 (2007).
Petrosillo et al., "Colistin monotherapy vs. combination therapy: evidence from microbiological, animal and clinical studies," Clin. Microbial. Infect., 14:816-827 (2008).
Quale et al., "Activity of polymyxin B and the novel polymyxin analogue CB-182,804 against contemporary gram-negative pathogens in New York City," Microbial Drug Resistance, 18:132-136 (2012).
Sato et al., "Des-fatty acyl-polymyxin B decapeptide analogs with antimicrobial activity specifically against Pseudomonas aeruginosa," Peptide Science, 44: 307-308 (2008).
Sato et al., "Novel des-fatty acyl-polymyxin B derivatives with Pseudomonas aeruginosa-specific antimicrobial activity," Chem. Phaim. Bull., 59:597-602 (2011).
Shechter et al., "N-[(2-Sulfo)-9-fluorenylmethoxycarbonyl]3-gentamicin C1 Is a long-acting prodrug derivative," J. Med. Chem., 45:4264-4270 (2002).
Vaara et al., "A novel polymyxin derivative that lacks the fatty acid tail and carries only three positive charges has strong synergism with agents excluded by the intact outer membrane," Antimicrob. Agents and Chemotherapy, 54:3341-3346 (2010).
Vaara et al., "Agents that increase the permeability of the outer membrane," Microbiological Reviews, 56:395-411 (1992).
Vaara et al., "Novel polymyxin derivatives carrying only three positive charges are effective antibacterial agents," Antimicrob. Agents and Chemotherapy, 52:3229-3236 (2008).
Vaara et al., "Susceptibility of carbapenemase-producing strains of Klebsiella pneumoniae and Escherichia coli to the direct antibacterial activity of NAB739 and to the synergistic activity of NAB7061 with rifampicin and clarithromycin," J. Antimicrob. Chemother, 65:942-945 (2010).
Voitenko et al., "Relationship between structure and histamine releasing action of polymyxin B and its analogues," Agents and Actions 30:153-156 (1990).
Weinstein et al., "Selective chemical modifications of Polymyxin B," Bioorganic and Medicinal Chemistry Letters, 8: 3391-3396 (1998).
Yamada et al., "Facile synthesis of N-alpha-protected-L-alpha,gamma-diaminobutyric acids mediated by polymer-supported hypervalent iodine reagent in water," J. Peptide Res., 64:43-50 (2004).
Yousef et al., "Melatonin attenuates colistin-induced nephrotoxicity in rats," Antimicrob. Agents Chemother., 55:4044-4049 (2011).
International Search Report and Written Opinion for PCT/GB2012/052844, dated Feb. 11, 2013.
Search Report issued in corresponding United Kingdom Patent Application No. GB1309248.1, dated Nov. 11, 2013.

* cited by examiner

COMPOUNDS

The present case claims the priority and benefit of U.S. 61/561,361 filed on 18 Nov. 2011 (18/11/2011), the contents of which are incorporated by reference herein in their entirety.

The present disclosure relates to novel compounds, pharmaceutical compositions comprising said compounds and the use of the said compounds and pharmaceutical compositions for treatment, for example treatment of microbial infections, particularly by Gram negative bacteria.

In susceptible individuals, certain Gram negative bacteria can cause serious complications and infections, such as pneumonia, urinary tract infections, wound infections, ear infections, eye infections, intra-abdominal infections, oral bacterial overgrowth and sepsis. The treatment of serious bacterial infections in clinical practice can be complicated by antibiotic resistance. Recent years have seen a rise in infections by Gram negative bacteria which are resistant to many types of antimicrobials including broad spectrum antibiotics such as aminoglycosides, cephalosporins and even carbapenems. There is therefore a need to identify new antimicrobials that are effective against Gram negative bacteria, in particular against multidrug resistant Gram negative bacteria.

Polymyxins are a class of antibiotics produced by the Gram positive bacterium *Bacillus polymyxa*. First identified in the late 1940s, polymyxins, particularly polymyxin B and polymyxin E (colistin) were used in the treatment of Gram negative infections. However, these antibiotics exhibited side effects such as nephrotoxicity. Consequently, their use in therapy is limited to treatment of last resort.

WO 2008/017734 tries to address this toxicity problem by providing polymyxin derivatives carrying at least two but no more than three positive charges. These compounds are said to be effective antibacterial agents with reduced toxicity. It is hypothesised in the disclosure that the reduced number of positive charges decreases the affinity of the compound for isolated rat kidney tissue which in turn may lead to a reduction in nephrotoxicity.

Surprisingly, the present inventors have found that certain alternative polymyxin type compounds including some with 4 or more charges have suitable antibacterial activity whilst also apparently exhibiting less toxicity, especially nephrotoxicity.

SUMMARY OF THE INVENTION

Thus there is provided a compound of the formula (I):

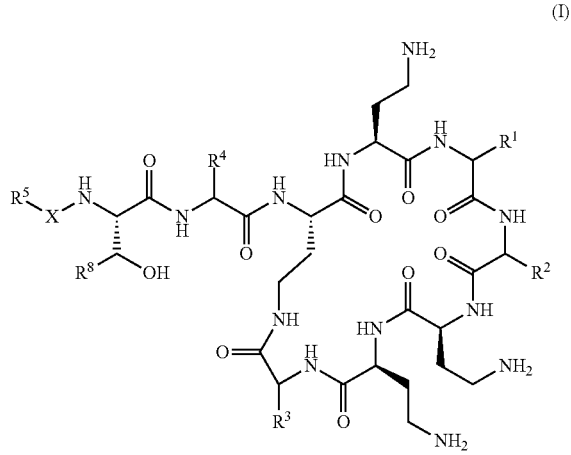

(I)

wherein:
X represents an —NHC(O)—, —C(O)—, —OC(O)—, —CH$_2$— or —SO$_2$—; and

R$^1$ together with the carbonyl group and nitrogen alpha to the carbon to which it is attached, represents a phenylalanine, leucine or valine residue;

R$^2$ together with the carbonyl group and nitrogen alpha to the carbon to which it is attached, represents a leucine, isoleucine, phenylalanine, threonine, valine or nor-valine residue;

R$^3$ together with the carbonyl group and nitrogen alpha to the carbon to which it is attached, represents a threonine or leucine residue;

R$^4$ together with the carbonyl group and nitrogen alpha to the carbon to which it is attached, represents α,γ-diaminobutyric acid or a serine residue;

R$^5$ represents
  C$_{0-12}$ alkyl(C$_{4-6}$ heterocyclyl), or
  C$_{2-12}$ alkyl or C$_{0-12}$ alkyl(C$_{3-8}$ cycloalkyl) wherein the alkyl or cycloalkyl bears:
    i) one, two or three hydroxyl groups, or
    ii) a —NR$^6$R$^7$ group, or
    iii) one —NR$^6$R$^7$ group and one or two hydroxyl groups;
R$^6$ represents hydrogen or C$_{1-4}$ alkyl; and
R$^7$ represents hydrogen or C$_{1-4}$ alkyl,
R$^8$ represents hydrogen or methyl, or
a pharmaceutically acceptable salt thereof.

The compounds of formula (I) are characterised in that the peptide part of the molecule contains only nine amino acids whereas natural polymyxins comprise 10 amino acids.

DETAILED DESCRIPTION

Surprisingly the compounds of formula (I) seem to have lower toxicity than the parent polymyxin compounds whilst retaining useful antibacterial activity.

It is known that polymyxin nonapeptide missing the acyl chain has reduced toxicity but lacks useful antibacterial activity. However, a study of chain lengths of simple acyl polymyxin B nonapeptide derivatives (K. Okimura et. al, *Bull. Chem. Soc. Jpn*, 2007, 80, 543) suggested the importance of chain length for antibacterial activity, with an optimum of around eight carbon atoms, and demonstrated that the acetyl derivative had very poor activity against *E. coli* and *Salmonella typhimurium*. This was consistent with conclusions from the acyl decapeptide series (P. C de Visser et al, *J. Peptide Res*, 2003, 61, 298), where the pentanoyl and butanoyl analogues showed a marked drop-off in activity.

We have surprisingly found good antibacterial activity together with reduced toxicity in polymyxin B nonapeptides according to the invention, including those substituted acyl nonapeptides with short acyl chains, especially those bearing an amino substituent.

It is suspected that the toxicity of polymyxin type compounds results from a detergent-like interaction with membranes of eukaryotic cells. In addition, nephrotoxicity of polymyxin type compounds may result from the fact that they are retained in kidney cells and thus accumulate rather than being excreted from the body. Whilst not wishing to be bound by theory it is hypothesised that the compounds of the present invention have a group R$^5$ which comprises a substituent which disrupts the hydrophobicity of the alkyl component thereof. The inventors believe that this disruption changes the balance of hydrophobic and hydrophilic nature of the molecules which means they are less well suited for aligning themselves in bilipid-layers which form membranes. In turn this inability to align in the membrane may result in lower residency time therein and thus may result in lower toxicity.

Polymyxin nonapeptide as employed herein is intended to refer to amino acids 2-10 of polymyxin B or polymyxin E.

An amino acid residue (for example a leucine residue, etc.) as employed herein is intended to refer to an amino acid that has lost a water molecule and forms a bond with another entity (such as another amino acid) through the carbonyl end thereof and also forms a bond through the nitrogen end thereof to another entity (such as another amino acid). The bonds formed may for example be amide bonds.

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkyl in the context of a linker molecule (i.e. substitute alkyl) clearly extends to alkylene fragments, including branched and straight chain versions thereof. Branches may terminate in alkyl radical such as —$CH_3$.

Heterocyclyl as employed herein is a saturated carbocyclic ring comprising at least one nitrogen ring atom, for example 1 or 2 nitrogen ring atoms, such as only 1 nitrogen ring atom and optionally containing a further ring heteroatom selected from oxygen and sulfur. Examples of $C_{4-6}$ heterocyclyl groups include azetidine, pyrrolidinyl, piperidinyl, piperazinyl and morpholinyl. In one embodiment the heterocyclyl is linked to the remainder of the molecule through nitrogen. In the term "$C_{4-6}$ heterocyclyl", the expression $C_{4-6}$ represents the total number of ring atoms, including carbon and heteroatoms.

In one embodiment $R^1$ together with the carbonyl group and nitrogen alpha to the carbon to which it is attached represents a phenylalanine residue, for example a D-phenylalanine or a leucine residue, such as a D-leucine residue.

In one embodiment $R^2$ together with the carbonyl group and nitrogen alpha to the carbon to which it is attached represents a leucine residue.

In one embodiment $R^3$ together with the carbonyl group and nitrogen alpha to the carbon to which it is attached represents a threonine residue.

In one embodiment $R^4$ together with the carbonyl group and nitrogen alpha to the carbon to which it is attached represents α,γ-diaminobutyric acid (Dab) or a serine residue, for example L-Dab or D-Ser.

In one embodiment X represents —C(=O).

In one embodiment $R^5$ represents azetidine, pyrrolidinyl or piperidinyl.

In one embodiment the $R^5$ $C_{2-12}$ alkyl component is $C_2$ alkyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl or $C_{12}$ alkyl.

In one embodiment $R^5$ $C_{2-12}$ alkyl component is $C_{3-10}$ alkyl, for example $C_{4-8}$ alkyl.

In one embodiment $R^5$ is $C_{3-8}$ cycloalkyl, for example $C_5$ cycloalkyl or $C_6$ cycloalkyl.

In one embodiment $R^5$ bears one substituent.

In one embodiment $R^5$ bears two substituents.

In one embodiment $R^5$ bears three substituents.

In one embodiment $R^5$ bears one, two or three hydroxyl groups, for example one hydroxyl group.

In one embodiment $R^5$ bears one amine group, for example a $C_{2-12}$ alkyl bearing one amine, such as $C_{2-4}$ alkyl bearing one amine.

In one embodiment $R^5$ bears one, two or three hydroxyl groups, such as one hydroxyl.

In one embodiment $R^5$ bears one amine group and one hydroxyl group.

In one embodiment $R^5$ bears one amine group and two hydroxyl groups.

In one embodiment wherein $R^5$ bears one or more hydroxyls then the alkyl chain is $C_{5-12}$.

In one embodiment $R^5$ does not bear more than one amine group.

In one embodiment wherein $R^5$ bears more than one substituent, the substituents are not located on the same carbon atom.

In one embodiment at least one $R^5$ substituent (such as one substituent) is located on $C_2$ alkyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl or $C_{12}$ alkyl.

In one embodiment at least one $R^5$ substituent (such as one substituent) is on a terminal carbon of a straight alkyl chain or an alkyl branch, for example a straight alkyl chain.

When the substituent is on the terminal carbon of a straight alkyl chain (or indeed the terminal carbon of a branch) the remaining part of the alkyl chain (or indeed the alkyl linking part of the branch) will form an alkylene link. Thus the term alkyl as used herein is in fact a generic term which covers the situation wherein part or all of the alkyl moiety is in fact an alkylene moiety.

Terminal carbon as employed herein is intended to refer to carbon that would be a —$CH_3$ if it bore no substituents.

In one embodiment at least one (such as only one) substituent is not on a terminal carbon, i.e. —CH(substituent)-.

In one embodiment $R^6$ is hydrogen.

In one embodiment $R^6$ is $C_{1-4}$ alkyl, such as $C_1$ alkyl, $C_2$ alkyl, $C_3$ alkyl or $C_4$ alkyl, for example methyl.

In one embodiment $R^7$ is hydrogen.

In one embodiment $R^7$ is $C_{1-4}$ alkyl such as $C_1$ alkyl, $C_2$ alkyl, $C_3$ alkyl or $C_4$ alkyl, for example methyl.

In one embodiment both $R^6$ and $R^7$ represent methyl.

In one embodiment $R^6$ represents H and $R^7$ represents methyl.

In one embodiment $R^5$ is selected from —CH(OH)(CH$_2$)$_5$CH$_3$, —CH$_2$NH$_2$, —CH$_2$CH$_2$NH$_2$, —CH$_2$CH$_2$CH$_2$NH$_2$, —(CH$_2$)$_5$NH$_2$, —(CH$_2$)$_7$NH$_2$, —CH$_2$CH$_2$NHCH$_3$, —CH$_2$CH$_2$N(CH$_3$)$_2$, and —(CH$_2$)$_7$OH.

In one embodiment $R^8$ is methyl.

In one embodiment $R^8$ is hydrogen.

In one embodiment, the compound is of formula (Ia):

(Ia)

or a pharmaceutically acceptable salt thereof.

Where $R^1$ (together with associated groups) represents phenylalanine, $R^2$ (together with associated groups) represents leucine, $R^3$ (together with associated groups) represents threonine, $R^4$ (together with associated groups) represents α,γ-diaminobutyric acid; and $R^8$ represents methyl (and together with the associated groups represents threonine), the compound of formula (Ia) is a polymyxin nonapeptide having amino acids 2-10 of polymyxin B.

Where $R^1$ (together with associated groups) represents leucine, $R^2$ (together with associated groups) represents leucine, $R^3$ (together with associated groups) represents threonine, $R^4$ (together with associated groups) represents α,γ-diaminobutyric acid; and $R^8$ represents methyl (and together with the associated groups represents threonine), the compound of formula (Ia) is a polymyxin nonapeptide having amino acids 2-10 of polymyxin E.

In one embodiment a compound of formula (I) has three positive charges.

In one embodiment a compound of formula (I) has four or five positive charges, such as four.

In one embodiment a compound of formula (I) has five positive charges.

In one embodiment a compound of formula (I) has six positive charges.

In one embodiment the compound is selected from:
2-Hydroxyoctanoyl polymyxin B nonapeptide;
2-Aminoethanoyl polymyxin B nonapeptide;
3-Aminopropanoyl polymyxin B nonapeptide;
3-(N,N-dimethylamino)-propanoyl polymyxin B nonapeptide;
4-Aminobutanoyl polymyxin B nonapeptide;
6-Aminohexanoyl polymyxin B nonapeptide;
8-Hydroxyoctanoyl polymyxin B nonapeptide;
8-Aminooctanoyl polymyxin B nonapeptide;
3-(N-methylamino) propanoyl polymyxin B nonapeptide;
2-Amino cyclopentane carbonyl polymyxin B nonapeptide;
3-Aminopropanoyl colistin (polymyxin E) nonapeptide;
3-Pyrrolidine-3-carbonyl polymyxin B nonapeptide;
3-Amino-3-cyclohexanepropanoyl] polymyxin B nonapeptide, or
a pharmaceutically acceptable salt thereof.

Additionally or alternatively, the compound is selected from:
5-Aminopentanoyl polymyxin B nonapeptide
Hydroxyacetyl polymyxin B nonapeptide
3-Hydroxyoctanoyl polymyxin B nonapeptide
4-(N,N-dimethylamino)-butanoyl polymyxin B nonapeptide
7-Aminoheptanoyl polymyxin B nonapeptide
4-Morpholinylbutanoyl polymyxin B nonapeptide
6-Hydroxyhexanoyl polymyxin B nonapeptide
3-Hydroxybutanoyl polymyxin B nonapeptide
4-(N-methylamino)-butanoyl polymyxin B nonapeptide,
trans-4-aminocyclohexanecarbonyl polymyxin B nonapeptide,
4-Aminobutanoyl polymyxin E nonapeptide,
2-Hydroxyoctanoyl polymyxin E nonapeptide,
cis-4-Aminocyclohexane carbonyl polymyxin B nonapeptide,
4-Amino-4-methyl pentanoyl polymyxin B nonapeptide
4-Amino-5-methylhexanoyl polymyxin B nonapeptide, including for example 4-(R)-Amino-5-methylhexanoyl polymyxin B nonapeptide
3-(1-Pyrrolidin-2-yl)-propionyl polymyxin B nonapeptide, including for example 3-(S)-(1-Pyrrolidin-2-yl)-propionyl polymyxin B nonapeptide
4-Aminopentanoyl polymyxin B nonapeptide, including for example 4-(S)-Aminopentanoyl polymyxin B nonapeptide
trans-4-Hydroxycyclohexanecarbonyl polymyxin B nonapeptide,
3-Hydroxypropanoyl polymyxin B nonapeptide
(2-Hydroxy-2-cyclohexyl)ethanoyl polymyxin B nonapeptide
2-Amino octanoyl polymyxin B nonapeptide, or
a pharmaceutically acceptable salt thereof.

Examples of salts of compound of formula (I) include all pharmaceutically acceptable salts, such as, without limitation, acid addition salts of strong mineral acids such as HCl and HBr salts and addition salts of strong organic acids such as a methanesulfonic acid salt. Further examples of salts include sulphates and acetates such as trifluoroacetate or trichloroacetate.

In one embodiment the compounds of the present disclosure are provided as a sulphate salt.

A compound of the disclosure can also be formulated as prodrug. Prodrugs can include an antibacterial compound herein described in which one or more amino groups are protected with a group which can be cleaved in vivo, to liberate the biologically active compound. In one embodiment the prodrug is an "amine prodrug". Examples of amine prodrugs include sulphomethyl, as described in e.g., Bergen et al, *Antimicrob. Agents and Chemotherapy,* 2006, 50, 1953 or $HSO_3$—FMOC, as described in e.g. Schechter et al, *J. Med Chem* 2002, 45(19) 4264, and salts thereof. Further examples of amine prodrugs are given by Krise and Oliyai in *Biotechnology: Pharmaceutical Aspects,* 2007, 5(2), 101-131.

In one embodiment the compounds of the invention are provided as a prodrug.

The disclosure herein extends to solvates of compounds of formula (I). Examples of solvates include hydrates.

The compounds of the disclosure include those where the atom specified is replaced by a naturally occurring or non-naturally occurring isotope. In one embodiment the isotope is a stable isotope. Thus the compounds of the disclosure include, for example deuterium containing compounds and the like.

The present invention provides compounds having amino acids 2-10 of polymyxin B, or a variant thereof as described below, wherein the N terminal of the amino acid corresponding to residue 2 in polymyxin B, is modified with a group $R^5$—X—. The variables $R^5$ and X are as defined above. In the compounds of the invention, residue 1 of polymyxin B is absent.

A variant of the compound is a compound in which one or more, for example, from 1 to 5, such as 1, 2, 3 or 4 amino acids are substituted by another amino acid. The amino acid is at a position selected from positions 2, 3, 6, 7 or 10 (referring to the numbering of residues used in polymyxin B). The substitution may be for another amino acid or for a stereoisomer.

At position 2, the variant may have a D-Ser substitution.
At position 3, the variant may have a Ser substitution.
At position 6, the variant may have a Leu or Val substitution.
A position 7, the variant may have a Ile, Phe, Thr, Val or Nva (norvaline) substitution.
At position 10, the variant may have a Leu substitution.
A polymyxin E compound may be regarded as a polymyxin B compound having a Leu substitution at position 6.

For convenience, the compounds of the invention are represented by the formula (I) where the amino acids at positions 2, 3, 6, 7 or 10 are determined by the nature of the groups $R^8$, $R^4$, $R^1$, $R^2$ and $R^3$ respectively. Compounds of the invention, which include the variants described above, are biologically active.

Compounds of formula (I) can be prepared by conventional peptide synthesis, using methods known to those skilled in the art. Suitable methods include solution-phase synthesis such as described by Yamada et al, *J. Peptide Res.* 64, 2004, 43-50, or by solid-phase synthesis such as described by de Visser et al, *J. Peptide Res,* 61, 2003, 298-306, and Vaara et al, *Antimicrob. Agents and Chemotherapy,* 52, 2008. 3229-3236. These methods include a suitable protection strategy, and methods for the cyclisation step. Alternatively, compounds may be prepared from readily available polymyxins, for example by removal of the N-terminal amino acid of the polymyxin (residue 1). Such a method is described herein for the preparation of compounds based on residues 2-10 of polymyxins B and E.

The invention also provides a method of preparing certain compound of formula (I) by reacting a compound of formula (II):

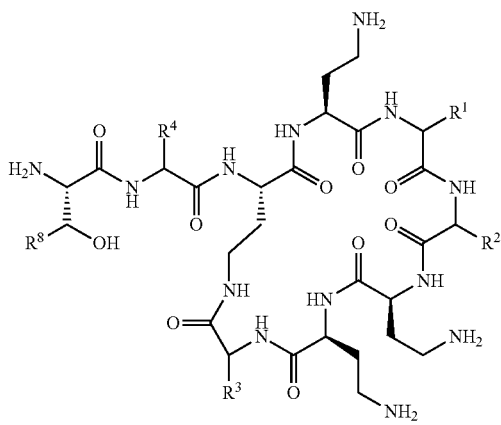

(II)

or a protected derivative thereof wherein:

$R^1$ together with the carbonyl group and nitrogen alpha to the carbon to which it is attached, represents a phenylalanine, leucine or valine residue;

$R^2$ together with the carbonyl group and nitrogen alpha to the carbon to which it is attached, represents a leucine, isoleucine, phenylalanine, threonine, valine or nor-valine residue;

$R^3$ together with the carbonyl group and nitrogen alpha to the carbon to which it is attached, represents a threonine or leucine residue;

$R^4$ together with the carbonyl group and nitrogen alpha to the carbon to which it is attached, represents α,γ-diaminobutyric acid or a serine residue;

with a compound of formula (III):

(III)

or a protected derivative thereof
wherein
$R^5$ is defined above for compounds of formula (I);
$X^1$ represents group which after coupling to compounds of formula (II) is converted or can be converted into —NHC(O)—, —C(O)—, —OC(O)—, —CH$_2$— or —SO$_2$; and
L represents a leaving group,
m represents 0 or 1, or
a pharmaceutically acceptable salt thereof,
optionally followed by deprotection to provide a compound of formula (I).

Generally compounds of formula (II) will be employed in a form where all the free amines, which are not desired to participate in the proposed reaction, are protected by a suitable protecting group for example tert-butyloxycarbonyl (BOC), 9-fluorenylmethoxycarbonyl (FMOC), or other suitable amine protecting group such as those described in "Protective groups in Organic Synthesis" by Theodora W. Green and Peter G. M. Wuts, Wiley, N.Y., 1999.

After the requisite chemical reactions deprotection to provide a compound of formula (I) can be carried out using standard methods such as those described in "Protective groups in Organic Synthesis" by Theodora W. Green and Peter G. M. Wuts, Wiley, N.Y., 1999.

In compounds of formula (I) wherein X represents —NHC(=O)—, can be synthesized employing a compound of formula (III) which corresponds to an isocyanate such as:

(Formula IIIa), wherein $R^5$ is defined above.

The reaction may be performed in a suitable solvent such as dichloromethane, optionally in the presence of base such as triethylamine or N-ethyldiisopropylamine (DIPEA).

Alternatively compounds of formula (I) wherein X represents —NHC(=O)—, can be synthesized employing a compound of Formula (IIIb):

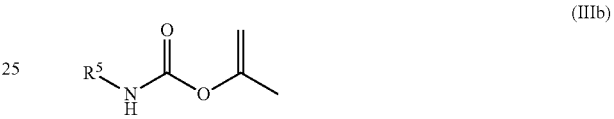

(IIIb)

wherein $R^5$ is defined above,
in the presence of base, as described in Gallon et al, *J. Org. Chem.,* 2005, 70, 6960.

In compounds of formula I wherein X represents —C(=O)—, —OC(=O)—, or —SO$_2$— can be synthesized employing a compound of formula (III) wherein $R^5$ is as hereinbefore described, $X^1$ represents —C(=O)—, —OC(=O)—, or —SO$_2$— and L represents a leaving group, for example Cl or Br.

The reaction may be performed in a suitable solvent, such as a polar aprotic solvent such as dichloromethane.

Compounds of formula (I) wherein X represent —C(=O)—, can be prepared employing a compound of formula (IIIc):

(IIIc)

wherein $R^5$ is defined above, for example in the presence of a coupling agent such as HATU, (O-(7-azabenzotriazol-1-yl)-N,N,N',N'-tetramethyluronium hexafluorophosphate), HBTU ((2-(1H-benzotriazole-1-yl)-1,1,3,3-tetramethyluronium hexafluorophosphate), DCC (dicyclohexyl carbodiimide), or PYBOP (benzotriazole-1-yl-oxy-tri-pyrrolidonophosphonium hexafluorophosphate), under basic conditions in a polar solvent.

Compounds of formula (I) wherein X represents —CH$_2$— can be prepared employing an aldehyde of formula (IIId):

(IIId)

wherein $R^5$ is as hereinbefore described, for example in the presence of a reducing agent such as sodium triacetoxyborohydride, sodium cyanoborohydride, or polymer-supported cyanoborohydride in a solvent such as methanol, dichloromethane, DMF, using conditions such as described in March's Advanced Organic Chemistry, Wiley, 2001.

In one aspect, the invention provides a pharmaceutical composition comprising a compound of formula (I), for example a therapeutically effective amount thereof and a pharmaceutically acceptable excipient, diluent and/or carrier (including combinations thereof).

The routes for administration (delivery) include, but are not limited to, one or more of: oral (e.g. as a dry powder/free flowing particulate formulation, tablet, capsule, or as an ingestible solution or suspension) buccal, sublingual.

The compositions of the disclosure include those in a form especially formulated for parenteral, oral, buccal, rectal, topical, implant, ophthalmic, nasal, rectal or genito-urinary use. In one aspect of the invention, the agents are delivered orally, hence, the agent is in a form that is suitable for oral delivery.

In some instances it may be possible to deliver the compounds of the disclosure by a topical, parenteral (e.g. by an injectable form) or transdermal route, including mucosal (e.g. as a nasal spray or aerosol for inhalation), nasal, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral).

There may be different composition/formulation requirements depending on the different delivery systems or different routes of administration. By way of example, the pharmaceutical composition of the present disclosure may be formulated to be delivered using a mini-pump or by a mucosal route, for example, as a nasal spray or aerosol for inhalation or ingestible solution, or parenterally in which the composition is formulated in an injectable form, for delivery by, for example, an intravenous, intramuscular or subcutaneous route. Alternatively, the formulation may be designed to be delivered by both routes. Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously.

For parenteral administration, the compositions may be best used in the form of a sterile aqueous solution which may contain other substances, for example enough salts or saccharides, in particular a monosaccharide, to make the solution isotonic with blood. Examples of parenteral administration include one or more of: intravenously, intraarterially, intraperitoneally, intrathecally, intraventricularly, intraurethrally, intrasternally, intracranially, intramuscularly or subcutaneously administering the agent, and/or by using infusion techniques.

In one embodiment the formulation of compounds of the invention is provided as a liposomal formulation. Liposomes can vary in size from low micrometer range to tens of micrometers, unilamellar liposomes are typically in the lower size range with various targeting ligands attached to their surface allowing for their surface-attachment and accumulation in pathological areas for treatment of disease. Liposomes are artificially prepared vesicles made of lipid bilayer In one embodiment the formulation is adapted for delivery by infusion or slow injection.

In one embodiment the formulation is adapted for delivery by bolus injection.

For buccal or sublingual administration the compositions may be administered in the form of tablets or lozenges which can be formulated in a conventional manner.

The compounds of the disclosure can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the disclosure may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents.

Solid compositions such as tablets, capsules, lozenges, pastilles, pills, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be administered in gelatin or HPMC (hydroxypropyl methylcellulose) capsules. Suitable excipients in this regard include microcrystalline cellulose, lactose, calcium carbonate, calcium sulphate, dibasic calcium phosphate and, mannitol, pregelatinised starch, corn starch, potato starch or high molecular weight polyethylene glycols.

For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Capsules may be filled with a powder (of medicament alone or as blend with selected filler(s)) or alternatively a liquid, each comprising one or more salts of the present disclosure and optionally a carrier. Where the capsule is filled with a powder the salts of the present disclosure and/or the carrier may be milled or micronised to provide material with an appropriate particle size.

Alternatively, the tablet or a capsule, as appropriate, may be filled into another capsule (preferably a HPMC capsule such as Capsugel®) to provide either a tablet in capsule or capsule in capsule configuration, which when administered to a patient yields controlled dissolution in the gastrointestinal tract thereby providing a similar effect to an enteric coating.

Thus in one aspect the disclosure provides a solid dose formulation of a salt of the present disclosure, for example where the formulation has an enteric coating.

In another aspect the disclosure provides a solid dose formulation comprising a protective capsule as outer layer, for example as a tablet in a capsule or a capsule in a capsule. The enteric coating may provide an improved stability profile over uncoated formulations.

The compounds of the disclosure may also be administered orally, in veterinary medicine, in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

In one embodiment the formulation is provided as a formulation for topical administration including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are preferably used, the use of lactose or glucose, particularly but not exclusively in the form of their hydrates.

Particles for deposition in the lung require a particle size less than 10 microns, such as 1-9 microns suitably from 0.1 to 5 µm, particularly preferably from 1 to 5 µm.

The propellant gases which can be used to prepare the inhalable aerosols are known from the prior art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellant gases may be used on their own or in mixtures thereof.

Particularly suitable propellant gases are halogenated alkane derivatives selected from among TG11, TG 12, TG 134a and TG227. Of the abovementioned halogenated hydrocarbons, TG134a (1,1,1,2-tetrafluoroethane) and TG227 (1,1,1,2,3,3,3-heptafluoro propane) and mixtures thereof are suitable for use in formulations of the present invention.

The propellant-gas-containing inhalable aerosols may also contain other ingredients such as co-solvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the disclosure may contain, for example, 0.002 to 5% by weight, 0.01 to 3% by weight, 0.015 to 2% by weight, 0.1 to 2% by weight, 0.5 to 2% by weight or 0.5 to 1% by weight of active.

The salts of the disclosure may also be used in combination with other therapeutic agents. The disclosure thus provides, in a further aspect, a combination comprising a salt of the present disclosure together with a further therapeutic agent. The combination may, for example be a combination of a salt of the compound of formula (I) and an antibiotic, such as vancomycin, fosfomycin, rifamycin, a beta-lactam (such as a cephalosporin or carbapenem), an aminoglycoside, a macrolide, a tetracyline, a lipopeptide, an oxazolidinone and/or an anti-inflammatory such as a steroid. The combination may be provided as a co-formulation or simply packaged together as separate formulations, for simultaneous or sequential delivery.

In one embodiment there is provided salts of the present disclosure in combination with a further therapeutic agent.

It is to be understood that not all of the compounds/salts of the combination need be administered by the same route. Thus, if the therapy comprises more than one active component, then those components may be administered by different routes.

The individual components of such combinations may be administered either sequentially or simultaneously in separate or combined pharmaceutical formulations by any convenient route. When administration is sequential, either the salt of the disclosure or the second therapeutic agent may be administered first. When administration is simultaneous, the combination may be administered either in the same or a different pharmaceutical composition.

The combinations referred to above may conveniently be presented for use in the form of a pharmaceutical formulation and thus pharmaceutical formulations comprising a combination as defined above together with a pharmaceutically acceptable carrier or excipient comprise a further aspect of the disclosure.

When combined in the same formulation it will be appreciated that the two compounds/salts must be stable and compatible with each other and the other components of the formulation. When formulated separately they may be provided in any convenient formulation, in such manner as are known for such compounds in the art.

The compositions may contain from 0.01-99% of the active material. For topical administration, for example, the composition will generally contain from 0.01-10%, more such as 0.01-1% of the active material.

When a salt of the disclosure is used in combination with a second therapeutic agent active against the same disease state the dose of each compound/salt may be the same or differ from that employed when the compound/salt is used alone. Appropriate doses will be readily appreciated by those skilled in the art. It will also be appreciated that the amount of a salt of the disclosure required for use in treatment will vary with the nature of the condition being treated and the age and the condition of the patient and will be ultimately at the discretion of the attendant physician or veterinarian.

Typically, a physician will determine the actual dosage which will be most suitable for an individual subject. The specific dose level and frequency of dosage for any particular individual may be varied and will depend upon a variety of factors including the activity of the specific salt employed, the metabolic stability and length of action of that salt, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses. For systemic administration the daily dose as employed for adult human treatment will range from 2-100 mg/Kg body weight, such as 5-60 mg/Kg body weight, which may be administered in 1 to 4 daily doses, for example, depending on the route of administration and the condition of the patient. When the composition comprises dosage units, each unit will preferably contain 100 mg to 1 g of active ingredient. The duration of treatment will be dictated by the rate of response rather than by arbitrary numbers of days.

In one embodiment the treatment regime is continued for 1, 2, 3, 4, 5, 6, 7, 8, 9, 10, 11, 12, 13, 14, 15, 16, 17, 18, 19, 20, 21 or more days.

As described above, the salts of the present disclosure may be employed in the treatment or prophylaxis of humans and/or animals.

There is further provided by the present disclosure a process of preparing a pharmaceutical composition, which process comprises mixing a salt of the disclosure or a pharmaceutically acceptable derivative thereof, together with a pharmaceutically acceptable excipient, diluent and/or carrier.

In another aspect, the invention provides a compound of formula (I) or a pharmaceutically acceptable salt thereof or a composition comprising the same for use in therapy, and in particular, in the treatment infection such as bacterial infection, such as a Gram negative bacterial infection.

In one embodiment the compounds and compositions of the disclosure are useful in the treatment of pneumonia, urinary tract infections, wound infections, ear infections, eye infections, intra-abdominal infections, bacterial overgrowth and/or sepsis.

In one embodiment the compounds are useful in the treatment of infections by bacteria which are multidrug resistant.

Examples of Gram negative bacteria include, but are not limited to, *Escherichia* spp., *Klebsiella* spp., *Enterobacter* spp., *Salmonella* spp., *Shigella* spp., *Citrobacter* spp., *Morganella morganii*, *Yersinia pseudotuberculosis* and other *Enterobacteriaceae*, *Pseudomonas* spp., *Acinetobacter* spp., *Moraxella*, *Helicobacter*, *Stenotrophomonas*, *Bdellovibrio*, acetic acid bacteria, *Legionella* and alpha-proteobacteria such as *Wolbachia* and numerous others. Other notable groups of Gram-negative bacteria include the cyanobacteria, spirochaetes, green sulfur and green non-sulfur bacteria.

Medically relevant Gram-negative cocci include three organisms, which cause a sexually transmitted disease (*Neisseria gonorrhoeae*), a meningitis (*Neisseria meningitidis*), and respiratory symptoms (*Moraxella catarrhalis*).

Medically relevant Gram-negative bacilli include a multitude of species. Some of them primarily cause respiratory problems (*Hemophilus influenzae*, *Klebsiella pneumoniae*, *Legionella pneumophila*, *Pseudomonas aeruginosa*), primarily urinary problems (*Escherichia coli*, *Enterobacter cloacae*), and primarily gastrointestinal problems (*Helicobacter pylori*, *Salmonella enterica*).

Gram-negative bacteria associated with nosocomial infections include *Acinetobacter baumannii*, which causes bacteremia, secondary meningitis, and ventilator-associated pneumonia in intensive-care units of hospital establishments.

In one embodiment the compounds and compositions of the present invention are useful in the treatment of infection of one or more of the following Gram negative bacteria: *E. coli, S. enterica, Klebsiella: K. pneumoniae, K. oxytoca; Enterobacter: E. cloacae, E. aerogenes, E. agglomerans, Acinetobacter: A. calcoaceticus, A. baumannii; Pseudomonas aeruginosa, Stenotrophomonas maltophila, Providencia stuartii, Proteus:, P. mirabilis, P. vulgaris.*

In one embodiment compounds of formula (I) or pharmaceutically acceptable salts thereof or compositions comprising the same are useful for the treatment of *Pseudomonas* infections including *P. aeruginosa* infection, for example skin and soft tissue infections, gastrointestinal infection, urinary tract infection, pneumonia and sepsis.

In one embodiment compounds of formula (I), or pharmaceutically acceptable salts thereof, or compositions comprising the same are useful for the treatment of *Acinetobacter* infections including *A. baumanii* infection, for pneumonia, urinary tract infection and sepsis.

In one embodiment compounds of formula (I), or pharmaceutically acceptable salts thereof, or compositions comprising the same are useful for the treatment of *Klebsiella* infections including *K. pneumoniae* infection, for pneumonia, urinary tract infection, meningitis and sepsis.

In one embodiment compounds of formula (I), or pharmaceutically acceptable salts thereof, or compositions comprising the same are useful for the treatment of *E. coli* infection including *E. coli* infections, for bacteremia, cholecystitis, cholangitis, urinary tract infection, neonatal meningitis and pneumoniae In one embodiment the compounds of formula (I) or pharmaceutically acceptable salts thereof or compositions comprising the same may be useful for long term treatment.

In one aspect there is provided a compound of formula (I) or a composition comprising the same for the manufacture of a medicament for one or more of the indications defined above.

In one aspect there is provided a method of treatment comprising the step of administering a therapeutically effective amount of a compound of formula (I) or a pharmaceutical acceptable salt thereof or a composition comprising the same to a patient (human or animal) in need thereof, for example for the treatment of an infection as described herein.

Where technically appropriate embodiments may be combined and thus the disclosure extends to all permutations/combinations of the embodiments provided herein.

Preferences given for compounds of formula (I) may equally apply to other compounds of the invention, disclosed herein, as technically appropriate.

| Abbreviation | Meaning |
|---|---|
| PMBN | Polymyxin B nonapeptide |
| Thr | Threonine |
| Ser | Serine |
| DSer | D-serine |
| Leu | Leucine |
| Ile | Isoleucine |
| Phe | Phenylalanine |
| DPhe | D-phenylalanine |
| Val | Valine |
| Dab | α,γ-Diaminobutyric acid |
| DIPEA | N,N-diisopropylethylamine |

EXAMPLES

Intermediate 1. Polymyxin B Nonapeptide

A mixture of Polymyxin B (20 g), immobilised papain (185 ELU/g), potassium phosphate buffer (25 mM; pH 7, 1.25 L), potassium chloride (30 mM), EDTA (10 mM) and cysteine (1 mM) was incubated at 37° C. for 18 h with gentle agitation. The progress of the reaction was monitored by LC-MS using the conditions outlined in Table 1. The immobilized papain was removed by filtration and the filtrate was concentrated in vacuo to leave a solid residue which was re-suspended in 10% aqueous methanol and left at room temperature overnight. The supernatant was decanted and concentrated in vacuo. Polymyxin B nonapeptide was purified from the residue by SPE on C18 silica, eluting with 0-10% aqueous methanol. Evaporation of the appropriate fractions gave the product as a white solid. m/z 482, $[M+2H]^{2+}$

TABLE 1

| LC-MS conditions Micromass Platform LC | | | |
|---|---|---|---|
| Column: | Zorbax 5µ C18 (2) 150 × 4.6 mm | | |
| Mobile Phase A: | 10% Acetonitrile in 90% Water, 0.15% TFA or 0.1% formic | | |
| Mobile Phase B: | 90% Acetonitrile in 10% Water, 0.15% TFA or 0.1% formic | | |
| Flow rate: | 1 mL/min | | |
| Gradient: | Time 0 min | 100% A | 0% B |
| | Time 10 min | 0% A | 100% B |
| | Time 11 min | 0% A | 100% B |
| | Time 11.2 min | 100% A | 0% B |
| | Time 15 min | 100% A | 0% B |
| Cycle time 15 min | | | |
| Injection volume: | 20 µL | | |
| Detection: | 210 nm | | |

Intermediate 2. tetra-(Boc) polymyxin B nonapeptide

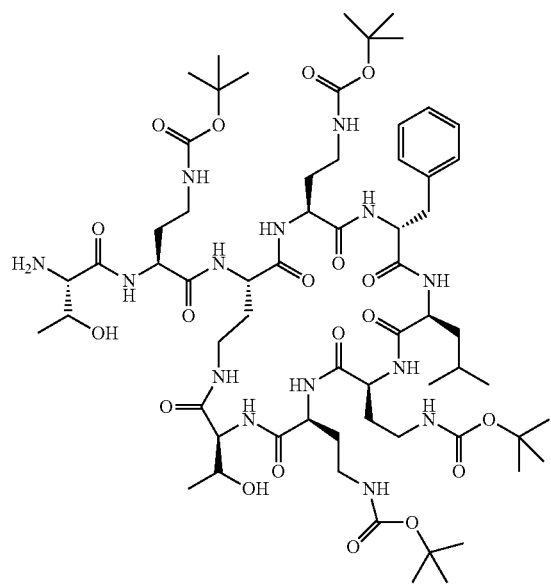

Molecular Weight = 1363.63
Exact Mass = 1362
Molecular Formula = C63H106N14O19

Selective BOC protection of the free γ-amino groups on the Dab residues of polymyxin B nonapaptide was carried out using the procedure of H. O'Dowd et al, *Tetrahedron Lett.,* 2007, 48, 2003-2005. Polymyxin B Nonapeptide (intermediate 1 7.5 g, 7.78 mmol) was suspended in water (65 mL) with sonication. Dioxane (65 mL) and triethylamine (65 mL) were added and the mixture was cooled in ice for 10 min prior to the addition of 1-(Boc-oxyimino)-2-phenyl acetonitrile (Boc-ON) (7.67 g; 31.15 mmol). The progress of the reaction was followed by LC-MS and reached completion after 30 minutes, whereupon the mixture was quenched by addition of 20% methanolic ammonia (50 mL). The liquid phase was decanted and the residual solid was purified by chromatography (eluent 0-20% methanol in dichloromethane) on silica gel to afford tetra-(Boc) polymyxin B nonapeptide as a white solid (2.5 g, 24%). TLC, $R_f$ 0.2 (10% methanol in dichloromethane). m/z 1362.8[MH]$^+$.

Intermediate 3. Colistin (Polymyxin E) nonapeptide

Colistin (polymyxin E, 5 g) was treated with immobilised papain (185 ELU/g), potassium phosphate buffer (25 mM; pH 7, 1.25 L), potassium chloride (30 mM), EDTA (10 mM) and cysteine (1 mM) at 37° C. for 32 h with gentle agitation to produce colistin (polymyxin E) nonapeptide. The progress of the reaction was monitored by LC-MS using the conditions outlined in Intermediate 1, Table 1. The immobilized papain was removed by filtration and the filtrate was concentrated in vacuo to leave a solid residue which was re-suspended in 10% aqueous methanol and left at room temperature overnight. The supernatant was decanted and concentrated in vacuo. Colistin (Polymyxin E) nonapeptide was purified from the residue by SPE on C18 silica (10 gm), eluting with 0-25% aqueous methanol. Evaporation of the appropriate fractions gave the product as a white solid. m/z 465.32 [M+2H]$^{2+}$.

Intermediate 4. tetra-(Boc) colistin (polymyxin E) nonapeptide

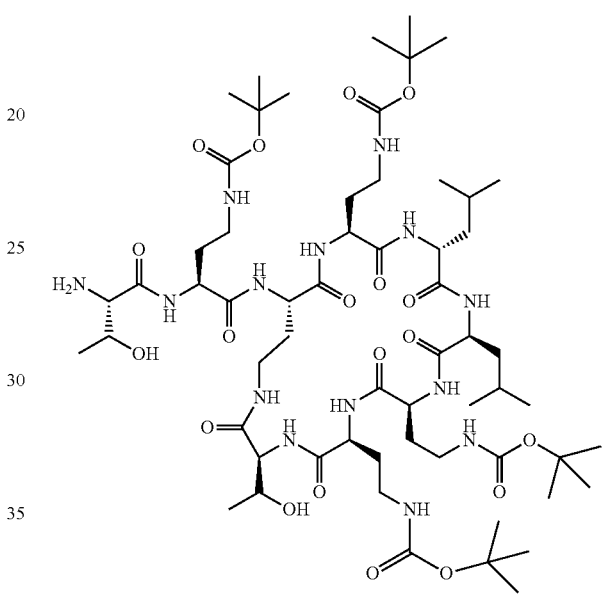

Molecular Weight = 1329.61
Exact Mass = 1328
Molecular Formula = C60H108N14O19

Colistin (Polymyxin E) Nonapeptide (2.5 g, 2.69 mmol) was suspended in water (35 mL) with sonication. Dioxane (35 mL) and triethylamine (35 ml) were added and the mixture was cooled in ice for 10 min prior to the addition of 1-(Boc-oxyimino)-2-phenyl acetonitrile (Boc-ON) (2.65 g; 10.76 mmol). The progress of the reaction was followed by LC-MS and reached completion after 10 minutes, whereupon the mixture was quenched by addition of 20% methanolic ammonia (25 mL). The liquid phase was decanted and the residual solid was re-dissolved in water and extracted sequentially with dichloromethane and iso-butanol. Based on LC-MS analysis, the decanted liquid and both dichloromethane and iso-butanol extracts were pooled together followed by concentration in vacuo to give yellow gum which was loaded onto flash chromatography (Si 60A- 35-70). The column was eluted with 0-20% methanol (containing 2% ammonia) in dichloromethane. The column fractions eluted with 7-10% methanol (containing 2% ammonia) in dichloromethane afforded tetra-(Boc) colistin (polymyxin E) nonapeptide as a white solid (1.18 g, 33%). m/z 1329.7 [M+H]$^+$.

Example 1
[2(R,S)-2-Hydroxyoctanoyl] Polymyxin B Nonapeptide, Trifluoroacetate
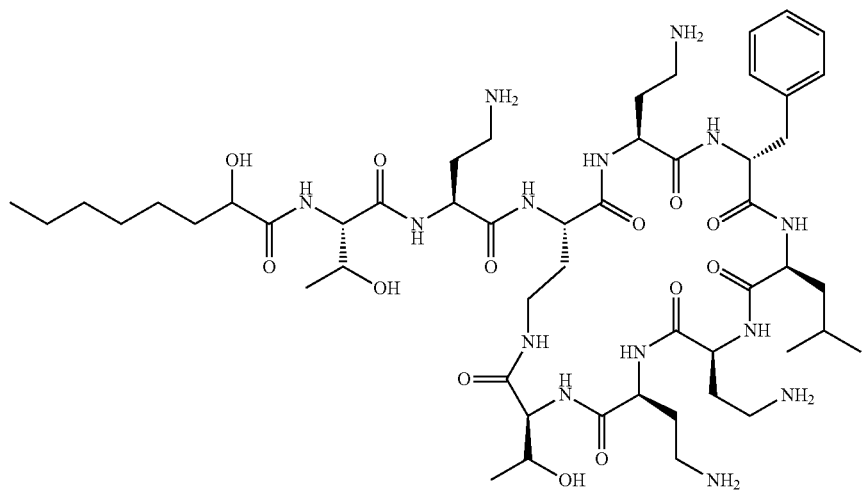
Molecular Weight = 1105.36
Exact Mass = 1104
Molecular Formula = C51H88N14O13
30
a) [2-(R,S)-2-Hydroxyoctanoyl] [tetra-(Boc)]-polymyxin B nonapeptide
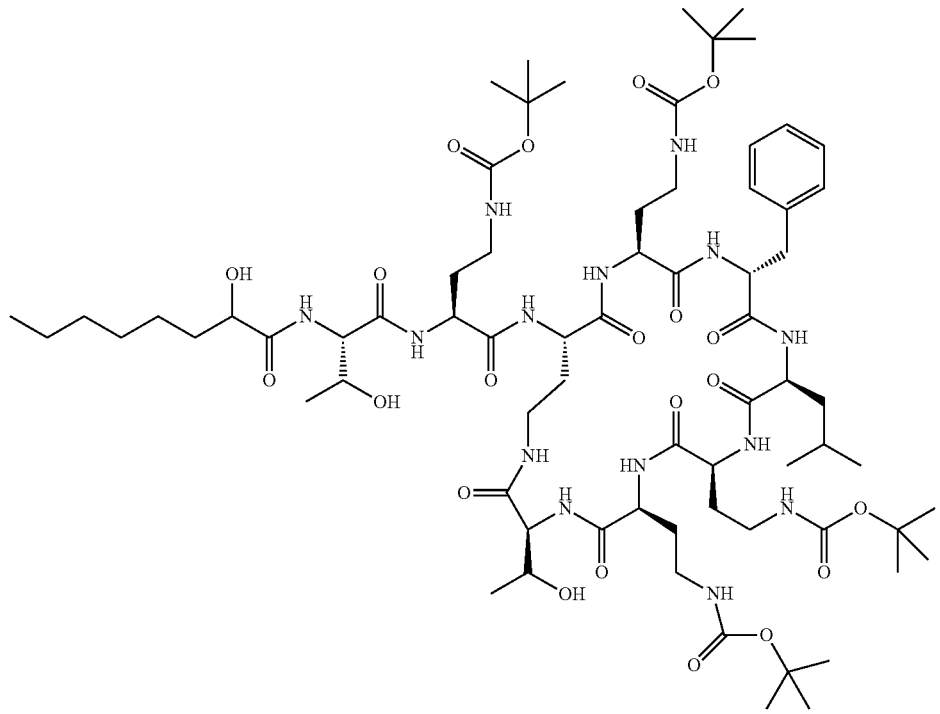
Molecular Weight = 1505.83
Exact Mass = 1504
Molecular Formula = C71H120N14O21

2-Hydroxyoctanoic acid (1.16 g, 7.34 mmol) was dissolved in dichloromethane (2 mL). N,N-Diisopropylethylamine (1.19 mL, 7.34 mmol) and 2-(1H-7-Azabenzotriazol-1-yl)-1,1,3,3-tetramethyl uronium hexafluorophosphate (HATU) (2.79 g, 7.34 mmol) were then added to the reaction mixture. After 30 min stirring at room temperature compound of intermediate 2 (2.0 g, 1.47 mmol) was added. After 16 h the completion of the reaction was confirmed by LC-MS and the reaction mixture was evaporated to dryness and purified using column chromatography on silica gel (eluent 0-10% methanol in dichloromethane). The appropriate fractions were concentrated to leave [2(R,S)-2-hydroxyoctanoyl] [tetra-(Boc)]-Polymyxin B nonapeptide as a colourless oil (1.28 g, 58%). TLC, $R_f$ 0.6 (10% MeOH in dichloromethane). m/z 1527.5, [M+Na]$^+$.

b) Title compound: [2(R,S)-2-Hydroxyoctanoyl] polymyxin B nonapeptide, trifluoroacetate 2-Hydroxyoctanoyl [tetra-(Boc)]-polymyxin B nonapeptide 1.28 g, 0.85 mmol) was dissolved in dichloromethane (2 mL). Trifluoroacetic acid (3.9 mL, 51.02 mmol) was added and the mixture was stirred at room temperature for 16 h, after which time LC-MS confirmed completion of the reaction. The reaction mixture was concentrated in vacuo to leave [2(R,S)-2-hydroxyoctanoyl] Polymyxin B nonapeptide, trifluoroacetate as a colourless oil (1.3 g, 93%). TLC, Rf baseline (10% MeOH in dichloromethane). m/z 1104.8 [MH]$^+$.

Example 2

[2(R,S)-2-Hydroxyoctanoyl] Polymyxin B Nonapeptide, Sulphate Salt

To the compound of Example 1 (1.3 g) was added water (1 mL) and the mixture was sonicated for 5 min. To the resulting suspension was added 1M NaHCO$_3$ (20 mL) until the mixture reached pH 9. The mixture was then passed through a 10 g C18 SPE column, eluting sequentially with 0, 40, 50, 60, 70, 80 and 100% aqueous methanol. LC-MS analysis of each fraction showed that the desired product eluted in the 60, 70 and 80% aqueous methanol fractions. These fractions were pooled and evaporated to leave a white solid (0.5 g), to which was added 0.1 M H$_2$SO$_4$ (30 mL) until pH 7 was reached. tert-Butanol (10 mL) was added and the mixture was stirred for 16 h at room temperature and subsequently freeze-dried to leave [2(R,S)-2-hydroxyoctanoyl] Polymyxin B nonapeptide, sulphate salt as a white solid (0.52 g). Analysis by HPLC according to the conditions outlined in Table 2 gave a retention time of 5.93 minutes. m/z 1104.9 [MH]$^+$.

TABLE 2

| Analytical HPLC conditions | |
|---|---|
| Column: | Zorbax 5µ C18 (2) 150 × 4.6 mm |
| Mobile Phase A: | 10% Acetonitrile in 90% Water, 0.15% TFA or 0.1% Formic acid |
| Mobile Phase B: | 90% Acetonitrile in 10% Water, 0.15% TFA or 0.1% Formic acid |
| Flow rate: | 1 mL/min |
| Gradient: | Time 0 min    100% A    0% B |
| | Time 10 min    0% A    100% B |
| | Time 11 min    0% A    100% B |
| | Time 11.2 min    100% A    0% B |
| Cycle time 15 min | |
| Injection volume: | 20 µL |
| Detection: | 210 nm |

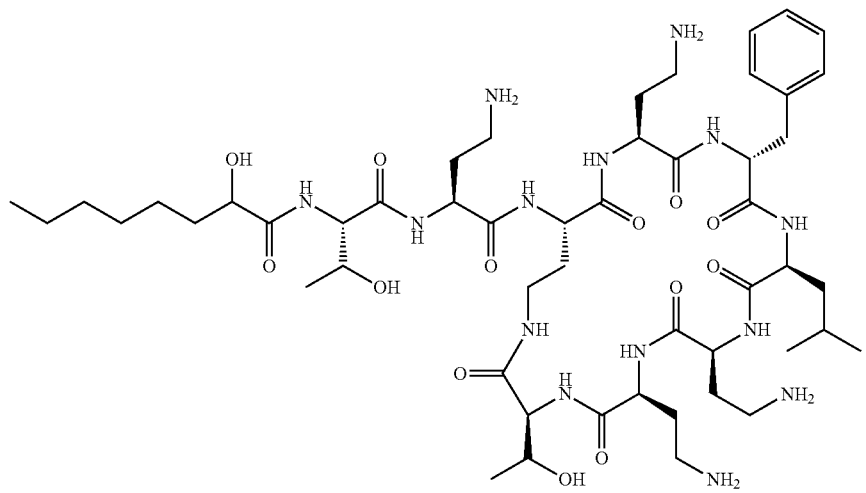

Molecular Weight = 1105.36
Exact Mass = 1104
Molecular Formula = C51H88N14O13

Example 3

2-Aminoethanoyl Polymyxin B Nonapeptide, Sulphate Salt

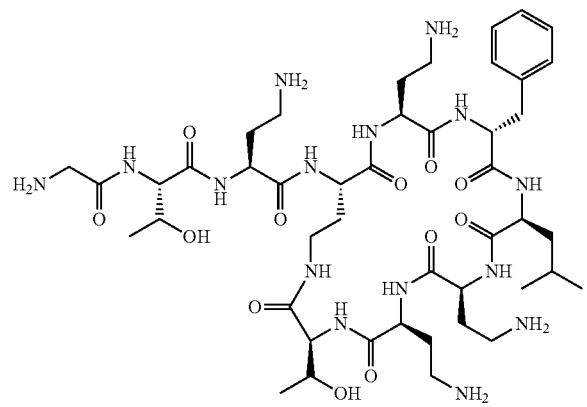 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CN)C(C)O)CCNC(=O)[C@H](C(C)O)NC(=O)[C@H](CCN)NC(=O)[C@H](CCN)NC1=O]

2-Aminoethanoyl polymyxin B nonapeptide, sulphate salt was prepared from tetra-(Boc) polymyxin B nonapeptide and 2-(tert-butoxycarbonylamino)-ethanoic acid following the sequence of reactions described for Examples 1 and 2. Retention time (HPLC) 4.99 min; m/z 1020.8 [MH]$^+$.

Example 4

3-Aminopropanoyl Polymyxin B Nonapeptide, Sulphate Salt

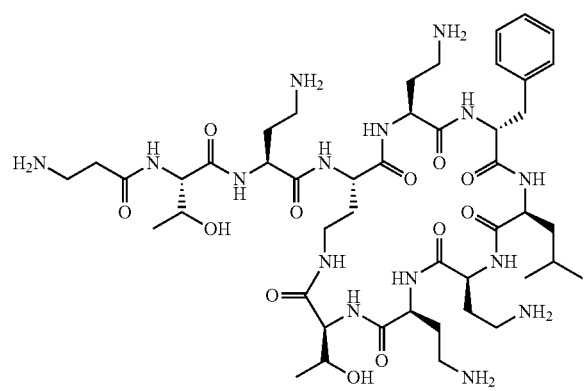 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCN)C(C)O)CCNC(=O)[C@H](C(C)O)NC(=O)[C@H](CCN)NC(=O)[C@H](CCN)NC1=O]

3-Aminopropanoyl polymyxin B nonapeptide, sulphate salt was prepared from tetra-(Boc) polymyxin B nonapeptide and 3-(tert-butoxycarbonylamino)-propanoic acid following the sequence of reactions described for Examples 1 and 2. Retention time (HPLC) 4.97 min; m/z 1034.42, [MH]$^+$.

Example 5

3-(N,N-dimethylamino)-propanoyl Polymyxin B Nonapeptide, Sulphate Salt

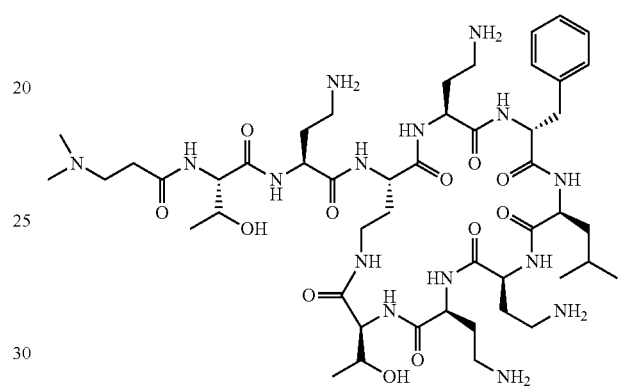

3-(N,N-dimethylamino)-propanoyl polymyxin B nonapeptide, sulphate salt was prepared from tetra-(Boc) polymyxin B nonapeptide and 3-(N,N-dimethylamino)propanoic acid following the sequence of reactions described for Examples 1 and 2. Retention time (HPLC) 5.01 min; m/z 531.92, [M+2H]$^{2+}$.

Example 6

4-Aminobutanoyl Polymyxin B Nonapeptide, Sulphate Salt

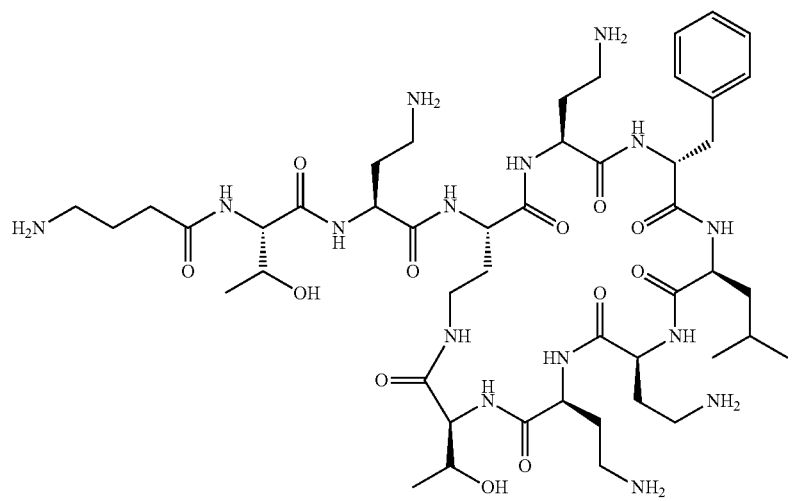 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCCN)C(C)O)CCNC(=O)[C@H](C(C)O)NC(=O)[C@H](CCN)NC(=O)[C@H](CCN)NC1=O]

4-Aminobutanoyl polymyxin B nonapeptide, sulphate salt was prepared from tetra-(Boc) polymyxin B nonapeptide and 4-(tert-butoxycarbonylamino)-butanoic acid following the sequence of reactions described for Examples 1 and 2. Retention time (HPLC) 4.97 min; m/z 524.91 [M+2H]$^{2+}$.

Example 7

6-Aminohexanoyl Polymyxin B Nonapeptide, Sulphate Salt

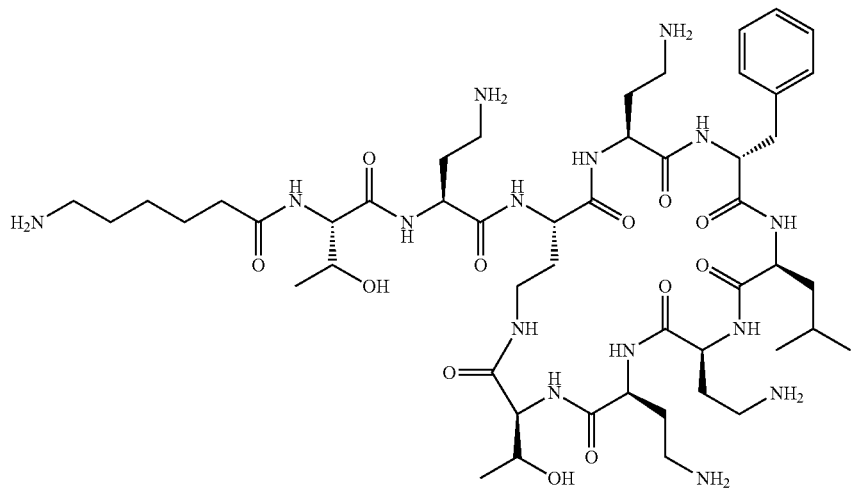 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCCCCN)C(C)O)CCNC(=O)[C@H](C(C)O)NC(=O)[C@H](CCN)NC(=O)[C@H](CCN)NC1=O]

6-Aminohexanoyl polymyxin B nonapeptide, sulphate salt was prepared from tetra-(Boc) polymyxin B nonapeptide and 6-(tert-butoxycarbonylamino)-hexanoic acid following the sequence of reactions described for Examples 1 and 2. Retention time (HPLC) 4.97 min; m/z 1077.15 [MH]$^+$.

Example 8

8-Hydroxyoctanoyl Polymyxin B Nonapeptide, Sulphate Salt

8-Hydroxyoctanoyl polymyxin B nonapeptide, sulphate salt was prepared from tetra-(Boc) polymyxin B nonapeptide and 8-hydroxyoctanoic acid following the sequence of reactions described for Examples 1 and 2. Retention time (HPLC) 5.29 min; m/z 1104.87, [M]$^+$.

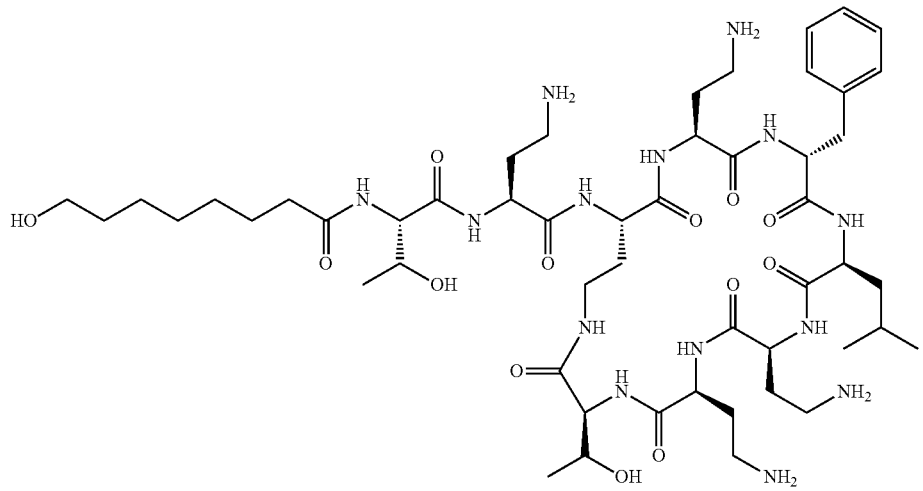 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCCCCCCO)C(C)O)CCNC(=O)[C@H](C(C)O)NC(=O)[C@H](CCN)NC(=O)[C@H](CCN)NC1=O]

Example 9

8-Aminooctanoyl Polymyxin B Nonapeptide, Sulphate Salt

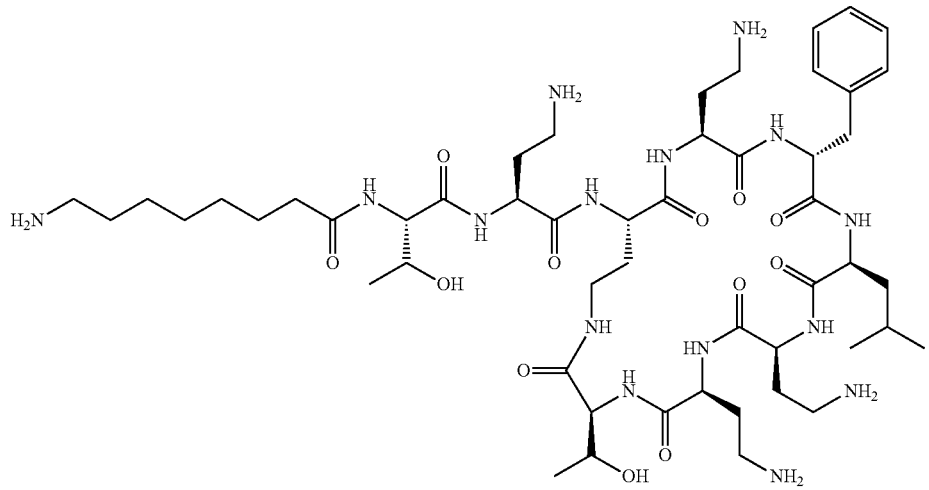 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCCCCCCN)C(C)O)CCNC(=O)[C@H](C(C)O)NC(=O)[C@H](CCN)NC(=O)[C@H](CCN)NC1=O]

8-Aminooctanoyl polymyxin B nonapeptide, sulphate salt was prepared from tetra-(Boc) polymyxin B nonapeptide and 8-(tert-butoxycarbonylamino)-octanoic acid following the sequence of reactions described for Examples 1 and 2. Retention time (HPLC) 5.02 min; m/z 1105.2, [MH]$^+$.

Example 10

3-(N-methylamino)Propanoyl Polymyxin B Nonapeptide, Sulphate Salt

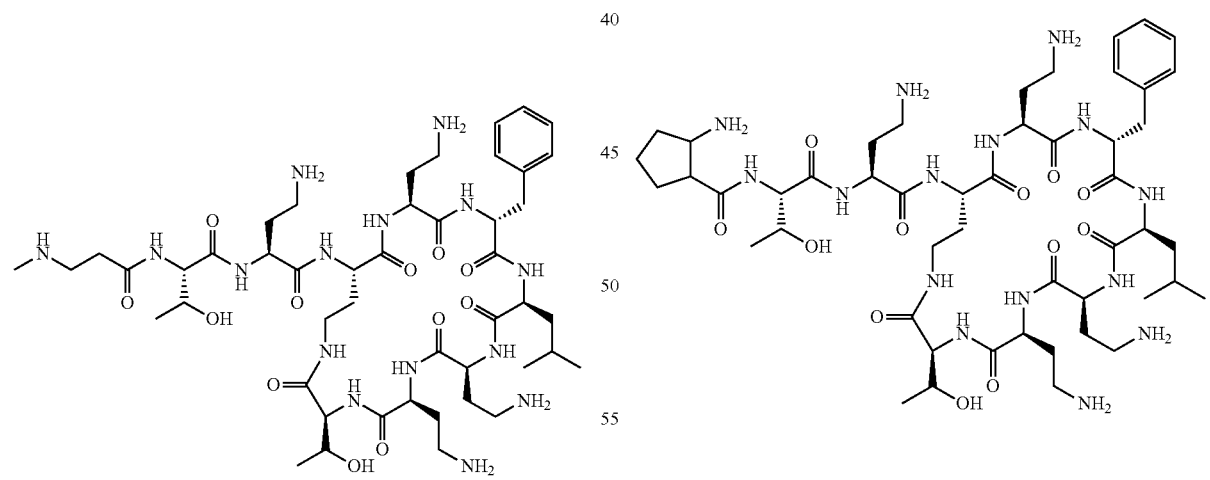

3-(N-Methylamino)propanoyl polymyxin B nonapeptide, sulphate salt was prepared from tetra-(Boc) polymyxin B nonapeptide and N-[(1,1-dimethylethoxy)carbonyl]-N-methyl β-Alanine, following the sequence of reactions described for Examples 1 and 2. Retention time (HPLC) 5.0 min; m/z 525.05, [M+2H]$^{2+}$.

Example 11

(1R,S/2R,S)-2-Aminocyclopentanecarbonyl Polymyxin B Nonapeptide, Sulphate Salt (1R,S/2R,S)-2-Aminocyclopentanecarbonyl polymyxin B nonapeptide, sulphate salt was prepared from tetra-(Boc) polymyxin B nonapeptide and cis-2-(tert-butoxycarbonylamino)-cyclopentane carboxylic acid following the sequence of reactions described for Examples 1 and 2. Retention time (HPLC) 5.07 min; m/z 1074.87, [MH]$^+$.

Example 12

3-Aminopropanoyl Colistin (Polymyxin E) Nonapeptide, Sulphate Salt

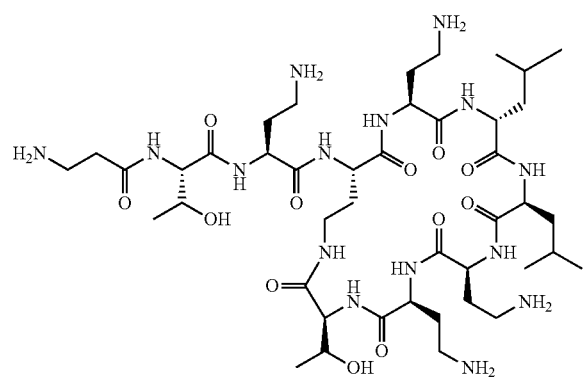 [SMILES: CC(C)C[C@@H]1NC(=O)[C@@H](CC(C)C)NC(=O)[C@H](CCN)NC(=O)[C@@H](NC(=O)[C@H](CCN)NC(=O)[C@@H](NC(=O)CCN)C(C)O)CCNC(=O)[C@H](C(C)O)NC(=O)[C@H](CCN)NC(=O)[C@H](CCN)NC1=O]

Following the sequential reactions described for Examples 1 and 2, 3-Aminopropanoyl colistin (polymyxin E) nonapeptide, sulphate salt was prepared from tetra-(Boc) colistin (polymyxin E) nonapeptide (Intermediate 4) and Boc-β-alanine. Retention (HPLC) time of 4.98 minutes. m/z 501, $[M+2H]^{2+}$.

Example 13

[3-(R,S)-Pyrrolidine-3-carbonyl] Polymyxin B Nonapeptide, Sulphate Salt

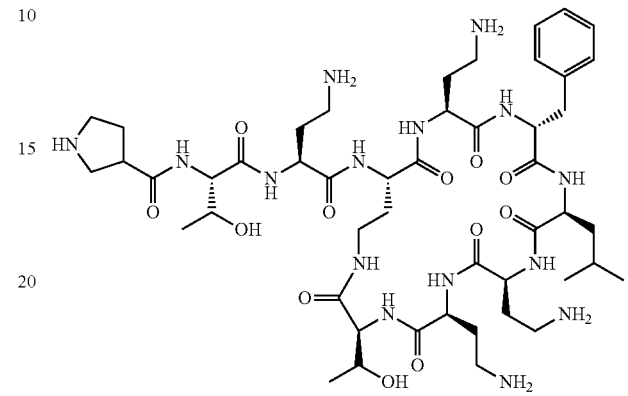

[3(R,S)-Pyrrolidine-3-carbonyl] polymyxin B nonapeptide, sulphate salt was prepared from tetra-(Boc) polymyxin B nonapeptide and 3-(N-tert-butoxycarbonyl)-pyrrolidinecarboxylic acid following the sequence of reactions described for Examples 1 and 2. Retention time (HPLC) 4.91 min; m/z 1060.58 $[MH]^+$.

Example 14

[3(R,S)-3-Amino-3-cyclohexanepropanoyl] Polymyxin B Nonapeptide, Sulphate Salt

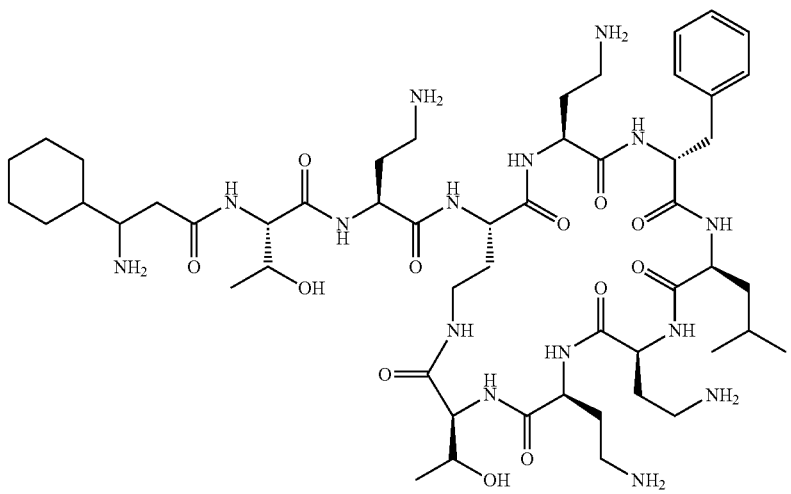 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CC(N)C2CCCCC2)C(C)O)CCNC(=O)[C@H](C(C)O)NC(=O)[C@H](CCN)NC(=O)[C@H](CCN)NC1=O]

[3(R,S)-3-Amino-3-cyclohexanepropanoyl polymyxin B nonapeptide, sulphate salt was prepared from tetra-(Boc) polymyxin B nonapeptide and 3-(tert-butoxycarbonylamino)-3-cyclohexanepropanoic acid following the sequence of reactions described for Examples 1 and 2. Retention time (HPLC) 5.24 min; m/z 1116.78, [MH]+.

Additional Examples 15-35

Additional compounds of Examples 15-35 were prepared using the methods of preparation set out for Examples 1 and 2 above. Thus, a compound having a substituent at the polymyxin B nonapeptide N terminal was prepared from tetra-(Boc) polymyxin B nonapeptide (intermediate 2) and an appropriate carboxylic acid in the presence of coupling agents (e.g. HATU) and base (e.g. DIPEA) (as set out in Example 1a), followed by treatment with acid (e.g. TFA) (as set out in Example 1a), and an appropriate work up (as set out in Example 2). Similarly, a compound having a substituent at the polymyxin E nonapeptide N terminal was prepared from tetra-(Boc) colistin (polymyxin E) nonapeptide (Intermediate 4) and an appropriate carboxylic acid in the presence of coupling agents (e.g. HATU) and base (e.g. DIPEA) (as set out in Example 1b), followed by treatment with acid (e.g. TFA) (as set out in Example 1b), and conversion to the sulphate salt (as set out in Example 2).

The additional compounds of Examples 15-35 are presented in Table 3 below.

The recorded retention times and masses given in the Table were obtained using the LC-MS conditions described above in Table 2.

The compounds were isolated as the sulphate salt forms of the compounds shown.

TABLE 3

| Ex. | Compound | Name | Formula and Predicted Mass | Retention Time (min) | m/z |
|---|---|---|---|---|---|
| 15 | | 5-Amino-pentanoyl polymyxin B nonapeptide | C48H83N15O12 1061.63 | 5.09 | 1062.7 (MH+) |
| 16 | | Hydroxy-acetyl polymyxin B nonapeptide | C45H76N14O13 1020.57 | 5.00 | 1021.1 (MH+) |

TABLE 3-continued

| Ex. | Compound | Name | Formula and Predicted Mass | Retention Time (min) | m/z |
|---|---|---|---|---|---|
| 17 | | 3-(R,S)-3-Hydroxy-octanoyl polymyxin B nonapeptide | C51H88N14O13 1104.67 | 6.04 | 1126.6 (M + Na+) |
| 18 | | 4-(N,N-dimethyl-amino)-butanoyl polymyxin B nonapeptide, | C49H85N15O12 1075.65 | 4.92 | 1076 (MH+) |
| 19 | | 7-Amino-heptanoyl polymyxin B nonapeptide | C50H87N15O12 1090.34 | 4.751 | 1091.76 (MH+) |
| 20 | | 4-Morpholinyl-butanoyl polymyxin B nonapeptide | C51H87N15O13 1117.66 | 5.08 | 1116.9 (M+) |

TABLE 3-continued

| Ex. | Compound | Name | Formula and Predicted Mass | Retention Time (min) | m/z |
|---|---|---|---|---|---|
| 21 | | 6-Hydroxy-hexanoyl polymyxin B nonapeptide | C49H84N14O13 1076.63 | 5.01 | 539 (M + 2H)$^{+2}$ |
| 22 | | 3-(R,S)-3-Hydroxy-butanoyl polymyxin B nonapeptide | C47H80N14O13 1048.60 | 4.83 | 525.3 (M + 2H)$^{+2}$ |
| 23 | | 4-(N-methyl-amino)-butanoyl polymyxin B nonapeptide | C48H83N15O12 1061.63 | 4.92 | 1062.4 (MH$^+$) |

TABLE 3-continued

| Ex. | Compound | Name | Formula and Predicted Mass | Retention Time (min) | m/z |
|---|---|---|---|---|---|
| 24 | | trans-4-aminocyclohexane-carbonyl polymyxin B nonapeptide | C50H85N15O12 1087.65 | 4.95 | 1087.1 (M⁺) |
| 25 | | 4-aminobutanoyl polymyxin E nonapeptide | C44H83N15O12 1013.63 | 4.94 | 1036.0 (MNa⁺) |
| 26 | | 2-(R,S)-2-Hydroxy-octanoyl polymyxin E nonapeptide | C48H90N14O13 1070.68 | 5.92 | 1071.3 (MH⁺) |

TABLE 3-continued

| Ex. | Compound | Name | Formula and Predicted Mass | Retention Time (min) | m/z |
|---|---|---|---|---|---|
| 27 | | cis-4-amino-cyclohexane carbonyl polymyxin B nonapeptide | C50H85N15O12 1087.65 | 5.27 | 1087.0 (M+) |
| 28 | | 4-Amino-4-methyl pentanoyl polymyxin B nonapeptide | C49H85N15O12 1075.65 | 5.08 | 1076.3 (MH+) |
| 29 | | 4-(R)-Amino-5-methyl-hexanoyl polymyxin B nonapeptide | C50H87N15O12 1089.67 | 5.16 | 1089.6 (M+) |

TABLE 3-continued

| Ex. | Compound | Name | Formula and Predicted Mass | Retention Time (min) | m/z |
|---|---|---|---|---|---|
| 30 | | 3-(S)-(1-pyrrolidin-2-yl)-propionyl polymyxin B nonapeptide | C50H85N15O12 1087.65 | 5.10 | 1087 (M+) |
| 31 | | 4-(S)-amino-pentanoyl polymyxin B nonapeptide | C48H83N15O12 1061.63 | 5.07 | 1062.1 (MH+) |
| 32 | | trans-4-hydroxycyclohexane-carbonyl polymyxin B nonapeptide | C50H84N14O13 1088.63 | 5.13 | 1088.7 (M+) |

TABLE 3-continued

| Ex. | Compound | Name | Formula and Predicted Mass | Retention Time (min) | m/z |
|---|---|---|---|---|---|
| 33 | | 3-Hydroxy-propanoyl polymyxin B nonapeptide | C46H78N14O13 1034.59 | 5.19 | 1034.3 (M+) |
| 34 | | 2-(R,S)-(2-Hydroxy-2-cyclohexyl) ethanoyl polymyxin B nonapeptide | C51H86N14O13 1103.65 | 5.80, 6.01 | 1103.9 (MH+) |
| 35 | | 2-(R,S)-2-Amino octanoyl polymyxin B nonapeptide | C51H89N15O12 1103.68 | 5.42, 5.79 | 1104.94 |

Antibacterial Activity

To evaluate the potency and spectrum of the compounds, susceptibility testing was performed against four strains of each of the four Gram negative pathogens, *Escherichia coli*, *Pseudomonas aeruginosa*, *Klebsiella pneumoniae* and *Acinetobacter baumannii*.

The day before testing, 3 to 4 colonies were picked from fresh Mueller-Hinton Agar (MHA) plate and transferred into 10 mL of Cation adjusted MHB (CaMHB). Cultures were incubated at 37° C. 250 rpm for 18-20 hours before being diluted 100-fold in fresh CaMHB. The subcultures were grown further until the $OD_{600}$ reached 0.2-0.3 corresponding to $10^5$-$10^6$ CFU/ml. The actively growing cultures were diluted 100-fold in fresh medium and used for the inoculum.

MIC testing was performed by two-fold serial antibiotic dilutions in CaMHB in sterile 96-well microtitre plates in a total volume of 170 μL (150 μL broth containing the antimicrobial agent, 20 μL inoculum). The assays were performed in duplicate. Plates were incubated aerobically without shaking for 18-20 hours at 37° C. with the MIC defined as the lowest concentration of drug that prevented visible growth.

Table 4 shows the MIC (micrograms/mL) of Examples 2 to 14 compared to Polymyxin B (PMB), Additional Studies on Antibacterial Activity Table 4A shows the MIC values obtained for compounds of Additional Examples 15 to 35 plus Examples 2, 6 and 14. Data was obtained under similar conditions to Table 4 except that different batches of cation-adjusted Muller-Hinton broth were used. The MIC values for these compounds are compared with those values obtained for Polymyxin B, Colistin Sulphate, CB-182,804 and NAB739 (as the TFA salt). CB-182,804 is a polymyxin decapeptide derivative with an aryl urea substituent at the N-terminus, which has been claimed to have lower toxicity than Polymyxin B (compound 5 in WO 2010/075416. See page 37). NAB739 has been described previously by Vaara et al.

TABLE 4

MIC Data for Compounds 2 to 14 (micrograms/mL)

| STRAIN | PMB | Eg2 | Eg3 | Eg4 | Eg5 | Eg6 | Eg7 | Eg8 | Eg9 | Eg10 | Eg11 | Eg12 | Eg13 | Eg14 |
|---|---|---|---|---|---|---|---|---|---|---|---|---|---|---|
| E. coli ATCC25922 | 0.5 | 1 | 2 | 2 | 1 | 0.5 | 2 | 2 | 2 | 0.5 | 2 | 4 | 0.5 | 0.5 |
| E. coli ATCC700928 | 0.25 | 0.25 | 4 | 0.06 | 0.5 | 0.125 | ND | 0.5 | 1 | 0.125 | 0.125 | ND | 0.25 | 0.25 |
| E. coli NCTC9001 | 0.25 | 0.25 | 4 | 0.25 | ND | 1 | 8 | 2 | 2 | 1 | 0.5 | ND | ND | ND |
| E. coli NCTC12900 | 0.125 | 0.25 | 8 | 1 | 2 | 2 | 4 | ND | 1 | 2 | 2 | ND | 2 | 0.5 |
| P. aeruginosa ATCC27853 | 0.5 | 0.5 | 0.5 | 0.125 | 0.25 | 0.25 | 0.5 | 0.5 | 0.5 | 0.06 | 0.125 | 0.5 | 0.25 | 0.5 |
| P. aeruginosa ATCC 9721 | 0.5 | 2 | 0.125 | 0.25 | 0.25 | 0.125 | ND | ND | 0.5 | 0.125 | 0.25 | ND | 0.125 | 0.25 |
| P. aeruginosa ATCC10145 | 0.5 | 1 | 0.25 | 0.5 | 0.5 | 0.25 | ND | 2 | 2 | 0.125 | 0.25 | ND | 0.5 | 0.25 |
| P. aeruginosa ATCCCRM-9027 | 0.25 | 0.25 | 0.125 | 0.25 | 0.5 | 0.125 | 0.25 | 0.25 | 0.5 | 0.125 | 0.125 | ND | 2 | 0.25 |
| K. pneumoniae ATCC 4352 | 0.5 | 0.5 | 1 | 0.125 | 0.25 | 0.125 | 0.5 | ND | 0.5 | 0.125 | 0.5 | 0.5 | 0.5 | 1 |
| K. pneumoniae ATCCBAA-1706 | 0.25 | 0.5 | 16 | 0.25 | 0.5 | 0.25 | 0.06 | ND | 0.5 | 0.25 | 0.25 | ND | 1 | 0.25 |
| K. pneumoniae NCTC7427 | 0.25 | 4 | 0.5 | 0.06 | 2 | 0.125 | 0.25 | 1 | 0.5 | 0.06 | 0.25 | ND | 0.25 | 0.25 |
| K. pneumoniae NCTC8172 | 0.5 | 4 | >32 | 2 | >32 | ND | >32 | ND | >32 | >32 | 2 | ND | 4 | 1 |
| A. baumannii ATCC19606 | 0.5 | 2 | 2 | 1 | 1 | 0.25 | ND | 16 | 0.125 | 2 | 32 | 0.5 | 0.5 |  |
| A. baumannii ATCCBAA-747 | 0.25 | 2 | >32 | 1 | 16 | ND | 8 | ND | >32 | 4 | 1 | ND | 4 | 0.5 |
| A. baumannii NCTC13423 | 0.25 | 1 | 16 | 1 | 16 | ND | 0.5 | ND | >32 | 2 | 0.5 | ND | 2 | 0.06 |
| A. baumannii NCTC7844 | 0.25 | 2 | 16 | 4 | 16 | 2 | 16 | 16 | >32 | 4 | 4 | ND | 4 | 0.5 |

ND: not determined

TABLE 4A

MIC Data for Additional Examples 15 to 35 plus Examples 2, 6 and 14 (micrograms/mL)

| STRAIN | PMB | Colistin Sulphate | CB108 804 | NAB739 TFA salt | 2 | 6 | 14 | 15 | 16 | 17 | 18 | 19 | 20 |
|---|---|---|---|---|---|---|---|---|---|---|---|---|---|
| E. coli ATCC25922 | 1 | 1 | 2 | 2 | 2 | 2 | 2 | 2 | 32 | 8 | 0.5 | 1 | 4 |
| E. coli NCTC9001 | 0.25 | 2 | ND | ND | 2 | 8 | 4 | 2 | ND | ND | ND | ND | ND |
| E. coli NCTC12900 | 0.25 | 0.5 | ND | ND | 8 | 8 | 4 | 2 | ND | ND | 4 | ND | ND |
| E. coli ATCC700928 | 0.25 | 0.25 | ND | ND | 0.5 | 2 | 2 | 1 | ND | ND | 0.25 | ND | ND |
| P. aeruginosa ATCC27853 | 0.5 | 0.5 | 1 | 1 | 0.5 | 0.25 | 0.25 | 0.25 | 0.25 | 2 | 0.125 | 0.25 | 1 |
| P. aeruginosa ATCC10145 | 1 | 0.5 | ND | ND | 1 | 0.5 | 0.5 | 1 | ND | ND | 0.25 | ND | ND |
| P. aeruginosa ATCC9721 | 0.125 | 0.5 | ND | ND | 0.5 | 0.125 | 0.25 | 0.125 | ND | ND | ND | ND | ND |
| P. aeruginosa AATCCRM 9027 | 0.25 | 0.5 | ND | ND | 0.5 | 0.25 | 0.125 | 0.125 | ND | ND | 2 | ND | ND |
| K. pneumoniae ATCC4352 | 0.25 | 0.125 | ND | 2 | 1 | 1 | 0.5 | 0.5 | 8 | 8 | 0.5 | 2 | >32 |
| K. pneumoniae NCTC7427 | 0.25 | 0.25 | ND | ND | 0.5 | 0.125 | 0.5 | 0.25 | ND | ND | 0.125 | ND | ND |
| K. pneumoniae NCTC8172 | 1 | 0.5 | ND | ND | 4 | 16 | >32 | 4 | ND | ND | >32 | ND | ND |
| K. pneumoniae ATCCBAA-1706 | ND | ND | ND | ND | ND | ND | ND | 0.5 | ND | ND | 8 | ND | ND |
| A. baumannii ATCC19606 | 0.125 | ND | 0.5 | 1 | 2 | 4 | ND | 1 | 32 | 4 | 1 | 16 | >32 |
| A. baumannii ATCCBAA-747 | 0.125 | 0.25 | ND | ND | 2 | ND | 0.5 | 8 | ND | ND | 16 | ND | ND |
| A. baumannii NCTC13423 | <0.06 | <0.06 | ND | ND | 1 | ND | 0.125 | 4 | ND | ND | 4 | ND | ND |
| A. baumannii NCTC7844 | 0.25 | 0.125 | ND | ND | 4 | 2 | 0.5 | 8 | ND | ND | 8 | ND | ND |

| STRAIN | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|
| E. coli ATCC25922 | 32 | 4 | 0.5 | 2 | 8 | 8 | 2 | 4 | 8 | 16 | >32 | 8 | >32 | 0.5 | ND |
| E. coli NCTC9001 | ND | ND | ND | ND | ND | ND | ND | ND | ND | ND | ND | ND | ND | 8 | ND |
| E. coli NCTC12900 | ND | ND | ND | ND | ND | ND | ND | ND | ND | ND | ND | ND | ND | 8 | ND |
| E. coli ATCC700928 | ND | ND | ND | ND | ND | ND | ND | ND | 2 | ND | ND | ND | ND | ND | ND |
| P. aeruginosa ATCC27853 | 1 | 0.5 | 0.25 | 0.125 | 4 | 4 | 0.125 | <0.06 | 0.125 | 0.125 | 0.25 | 0.125 | 0.5 | 0.125 | 0.25 |
| P. aeruginosa ATCC10145 | ND | ND | ND | ND | ND | ND | ND | ND | 0.5 | ND | ND | ND | ND | 0.5 | ND |
| P. aeruginosa ATCC9721 | ND | ND | ND | ND | ND | ND | ND | ND | 0.25 | ND | ND | ND | ND | 0.25 | ND |
| P. aeruginosa AATCCRM 9027 | ND | ND | ND | ND | ND | ND | ND | ND | 0.5 | ND | ND | ND | ND | 0.5 | ND |
| K. pneumoniae ATCC4352 | 32 | 8 | 0.5 | 0.125 | 4 | 8 | 0.125 | 0.25 | 0.5 | 1 | 0.5 | 4 | 4 | 1 | 1 |
| K. pneumoniae NCTC7427 | ND | ND | ND | ND | ND | ND | ND | ND | 0.5 | ND | ND | ND | ND | 0.5 | ND |
| K. pneumoniae NCTC8172 | ND | ND | ND | ND | ND | ND | ND | ND | >32 | ND | ND | ND | ND | >32 | ND |
| K. pneumoniae ATCCBAA-1706 | ND | ND | ND | ND | ND | ND | ND | ND | ND | ND | ND | ND | ND |  | ND |
| A. baumannii ATCC19606 | >32 | >32 | 8 | 2 | 16 | 16 | 0.5 | 4 | 2 | 8 | 8 | 16 | >32 | 1 | 2 |
| A. baumannii ATCCBAA-747 | ND | ND | ND | ND | ND | ND | ND | ND | 1 | ND | ND | ND | ND | 1 | ND |
| A. baumannii NCTC13423 | ND | ND | ND | ND | ND | ND | ND | ND | 0.5 | ND | ND | ND | ND | 0.25 | ND |
| A. baumannii NCTC7844 |  | ND | ND | ND | ND | ND | ND | ND | 2 | ND | ND | ND | ND | 2 | ND |

ND: not determined

The in vitro antibacterial activities of the compounds of examples 2 and 6 were evaluated against a panel of 500 Gram-negative bacterial isolates alongside Colistin. The panel consisted of 100 clinical isolates of each of *A. baumannii, E. coli, K. pneumoniae* and *P. aeruginosa*. The panel represented the current epidemiology in Europe and the USA and included a number of relevant strains with defined resistant phenotypes to current clinically-used antibacterial agents. These resistant strains included 20 *A. baumannii*, 22 *E. coli*, 25 *K. pneumoniae* and 20 *P. aeruginosa* strains.

The results of the study are summarised in Table 4B. All compounds were tested up to a maximum concentration of 64 μg/mL with the exception of colistin, which was evaluated up to a maximum concentration of 16 μg/mL.

TABLE 4B

Summary of the MIC values (μg/mL) of Examples 2 and 6, and Colistin against a panel of 400 Gram-negative clinical isolates and 100 Gram negative strains of defined resistant phenotypes

| Example | Organism | Range Clinical isolates | Range Resistant strains | $MIC_{50}$ Clinical isolates | $MIC_{50}$ Resistant strains | $MIC_{90}$ Clinical isolates | $MIC_{90}$ Resistant strains |
|---|---|---|---|---|---|---|---|
| Colistin | A. baumannii | 0.5-4 | 1-4 | 2 | 2 | 2 | 2 |
| | E. coli | 0.5-4 | 0.25-2 | 2 | 1 | 2 | 1 |
| | K. pneumoniae | 1-16 | 1->16 | 2 | 2 | 4 | 8 |
| | P. aeruginosa | 0.25-4 | 0.5-2 | 2 | 2 | 4 | 2 |
| 2 | A. baumannii | 1-32 | 2-4 | 4 | 4 | 8 | 4 |
| | E. coli | 1-16 | 0.5-4 | 2 | 1 | 4 | 2 |
| | K. pneumoniae | 2->64 | 2->64 | 8 | 8 | 32 | 32 |
| | P. aeruginosa | 1-8 | 1-4 | 2 | 2 | 4 | 4 |
| 6 | A. baumannii | 0.5->64 | 1-4 | 2 | 2 | 8 | 4 |
| | E. coli | 0.12->64 | 0.06-4 | 2 | 0.5 | 8 | 4 |
| | K. pneumoniae | 0.5->64 | 1->64 | >64 | >64 | >64 | >64 |
| | P. aeruginosa | 0.06-64 | 0.12-16 | 0.25 | 0.5 | 16 | 8 |

In vivo Efficacy Against *E. coli* Thigh Infection in Mice

The in vivo efficacy of 8 compounds of the invention (Examples 2, 4, 5, 6, 7, 8, 10, and 11) was evaluated in a mouse thigh infection model of *E. coli*. The results are summarized in Table 5.

Groups of 5 female specific-pathogen-free CD-1 mice weighing 22±2 g were used. The animals were made neutropenic by intraperitoneal administration of cyclophosphamide on days −4 (150 mg/kg) and −1 (100 mg/kg). On Day 0, animals were inoculated intramuscularly with $10^5$ CFU/mouse of *Escherichia coli* isolate ATCC25922 into the right thigh. At 1 h, the CFU count was determined from 5 mice and the remaining mice (five per group) were treated with a subcutaneous injection of the drug at +1 and 6 hr post-infection. In each study, there were two dose groups per test compound, 1.5 and 5 mg/kg BID, respectively. Examples 2, 4, 5, 6, 7, 8, 10, 11 and polymyxin B were prepared in Normal Saline at 2 mg/mL and the solution was adjusted to pH 6-7 by addition of 0.1M $H_2SO_4$ or 4.2% $NaHCO_3$ as required. Twenty-four hours after infection, the mice were euthanized humanely. The muscle of the right thigh of each animal was harvested, homogenized, serially diluted and plated on Brain Heart Infusion agar+0.5% charcoal (w/v) for CFU determination. Decrease of the total CFU of right thigh as compared to control counts at 24 hrs post-infection was determined for each dose group. The compounds 2 and 6 at 10 mg/kg/day demonstrated an efficacy comparable to that of polymyxin B with over 3 $log_{10}$ reduction in bacterial counts.

TABLE 5

In vivo Efficacy Versus *E. coli* ATCC25922 Thigh Infections in Neutropenic Mice

| Example No | Total daily dosage (mg/kg) | Mean $log_{10}$ CFU reduction vs. control |
|---|---|---|
| Polymyxin B | 3 | 2.5 [a] |
| | 10 | 4.2 [a] |
| 2 | 3 | 0.98 [b] |
| | 10 | 4.48 [b] |
| 4 | 3 | 0 [b] |
| | 10 | 0.82 [b] |
| 5 | 3 | 0.52 |

TABLE 5-continued

In vivo Efficacy Versus *E. coli* ATCC25922 Thigh Infections in Neutropenic Mice

| Example No | Total daily dosage (mg/kg) | Mean $log_{10}$ CFU reduction vs. control |
|---|---|---|
| | 10 | 0.51 |
| 6 | 3 | 0.72 [b] |
| | 10 | 3.38 [b] |
| 7 | 3 | 1.09 |
| | 10 | 2.15 |
| 8 | 3 | 0.53 |
| | 10 | 0.82 |
| 10 | 3 | 0.17 |
| | 10 | 0.56 |
| 11 | 3 | 1.19 |
| | 10 | 1.85 |

[a] mean values of 5 independent studies;
[b] mean value of 2 independent studies.

Additional Studies on the In vivo Efficacy Against *E. coli* Thigh Infection in Mice The in vivo efficacy of the compound of Example 14 was evaluated in a mouse thigh infection model of *E. coli*. using the methods described in the examples above. The result is summarized in Table 5A in comparison with Polymyxin B.

TABLE 5A

In vivo Efficacy Versus *E. coli* ATCC25922
Thigh Infections in Neutropenic Mice

| Example No | Total daily dosage (mg/kg) | Mean log₁₀ CFU reduction vs. control |
|---|---|---|
| Polymyxin B | 3 | 3.75 |
|  | 10 | 4.87 |
| 14 | 3 | 0 |
|  | 10 | 4.05 |

Compounds 14 at 10 mg/kg/day demonstrated an efficacy comparable to that of polymyxin B with over 3 $\log_{10}$ reduction in bacterial counts.

Additional Studies on the In vivo Efficacy Against *Klebsiella pneumoniae* Thigh Infection in Mice Using the same procedure as described above, the in vivo efficacy of three compounds of the invention (Examples 2, 6, and 14) was evaluated in a mouse thigh infection model of *Klebsiella pneumoniae* ATCC10031, using Colistin (Polymyxin E) as comparator. The results are summarized in Table 5B. The compounds 2, 6 and 14 at 10 mg/kg/day demonstrated an efficacy comparable to that of Colistin with approx. 2 $\log_{10}$ reduction in bacterial counts.

TABLE 5B in vivo efficacy versus *K. pneumoniae* ATCC10031
thigh infections in neutropenic mice.

| Example | Total daily dosage (mg/Kg) | Mean log₁₀ CFU reduction vs. control |
|---|---|---|
| Colistin | 10 | 2.60 |
| 2 | 10 | 2.22 |
| 6 | 10 | 1.92 |
| 14 | 10 | 2.30 |

Pharmacokinetic and Urinary Clearance Studies

The pharmacokinetics and urinary clearance of 3 compounds (Examples 2, 4 and 6) of the invention and polymyxin B were evaluated in rats.

Drug solutions were prepared at 4 mg/mL in Normal Saline and the pH adjusted to 6-7 by adding the appropriate volume of 0.1 M $H_2SO_4$ or 4.2% $NaHCO_3$. The solutions were filter-sterilized and stored at −80° C. before use. On the day of the experiment, drug solutions were diluted to 1 mg/mL with sterile Normal Saline.

Groups of 3 male Sprague Dawley rats were acclimatised for a minimum of 4 days before the study. Rats were anesthetized using isofluorane and a cannula was inserted into the jugular vein. One day after surgery, rats were dosed with an intravenous bolus injection of the solution at 1 mg/kg through the cannula, followed by washing with Normal Saline. Blood was collected manually through the cannula prior to administration of the compound and at 0.08, 0.25, 0.5, 1, 3, 6, 8 and 24 h thereafter. Plasma was harvested by centrifugation immediately after blood collection. Twenty-four hour urine samples were collected prior to and after administration of the compound in 0-4 h, 4-6 h, and 6-24 h intervals. Plasma and urine samples were frozen at −20° C.

Determination of the plasma and urine concentrations of the drug was performed by Liquid Chromatography Mass Spectrometry (LC-MS/MS). Before analysis the plasma and urine samples were prepared as follows. Plasma samples were thawed on the day of analysis and mixed with 3 volumes of acetonitrile containing 0.1% (v/v) formic acid and 100 ng/mL of internal standard. After centrifugation, supernatants were transferred to a 96-well plate and diluted 1:1 with water ready for analysis by LC-MS/MS. Urine samples were purified by solid-phase extraction (SPE) on Oasis HLB cartridges (Waters, UK) eluting with 100% methanol. An aliquot was transferred to a 96 well plate and diluted 1:1 with water before addition of internal standard solution, ready for analysis by LC-MS/MS.

| | |
|---|---|
| Column: | Kinetex 2.6 μm XB-C18 50 × 2.1 mm |
| Mobile Phase A: | Water + 0.15% TFA or 0.1% formic acid |
| Mobile Phase B: | Acetonitrile + 0.15% TFA or 0.1% formic acid |
| Flow rate: | 0.5 mL/min |
| Gradient: | |
| Time 0 min | 95% A    5% B |
| Time 1.20 min | 5% A    95% B |
| Time 1.50 min | 5% A    95% B |
| Time 1.51 min | 95% A    5% B |
| Time 3.00 min | 95% A    5% B |
| Cycle time 4.5 min | |
| Injection volume: | 20 μL |

The pharmacokinetic parameters were determined by non-compartmental analysis using WinNonLin v5.3. The urinary recovery was recorded as the percentage of intact drug recovered in the urine for the first 24 h after injection.

TABLE 6

Pharmacokinetics of polymyxin B and PMBN derivatives

| Example No | $t_{1/2}$ (hr) | $C_{max}$ (ng/mL) | $AUC_{0\text{-}inf}$ (ng·hr/mL) | Cl (mL/hr/kg) | Vd (mL/kg) | Urinary recovery (% dose) |
|---|---|---|---|---|---|---|
| Polymyxin B | 1.94 | 1455 | 2372 | 429 | 1120 | 0.3 |
| 2 | 1.34 | 2400 | 4009 | 251 | 488 | 0.5 |
| 4 | 1.33 | 2524 | 2033 | 492 | 690 | 3.9 |
| 6 | 0.56 | 3581 | 2619 | 386 | 289 | 8.9 |

Interestingly, all compounds show higher urinary recovery than polymyxin B. Previous studies reported that polymyxin E (colistin) undergoes extensive renal tubular reabsorption (Li et al., *Antimicrob. Agents and Chemotherapy*, 2003, 47(5); Yousef et al., *Antimicrob. Agents and Chemotherapy*, 2011, 55(9)). Whilst not wishing to be bound by theory, higher urinary clearance of the compounds could reflect a decreased renal tubular reabsorption which could in turn reduce their nephrotoxicity potential.

In vitro Renal Cell Toxicity Assay

The renal cell toxicity of the compounds was assessed in an in vitro assay using the HK-2 cell line, an immortalized proximal tubule cell line derived from a normal human kidney. The endpoint to describe the toxicity of the compounds was the reduction of resazurin correlating with the metabolic activity of the cells.

Cells were cultured in 150 cm² flasks in 25 mL supplemented KSF (with 5 ng/mL EGF and 50 μg/mL BPE). Cells were maintained at 70% confluence with a maximum of 25 passages. Day 1: Media was removed and cells were washed with 10 ml DPBS. Six ml of a 0.25% trypsin solution with EDTA was then added to the flask and the cells returned to the incubator. After 1 to 2 minutes incubation, 14 ml media was added to the flask to inactivate the trypsin. The cell suspension was transferred to a centrifuge tube and the cells pelleted at 1000 rpm for 6 minutes. The cell pellet was then resuspended in fresh media supplemented with EGF and BPE. The cell number was counted and cells were diluted to 46875 cells/mL in fresh medium supplemented with EGF and BPE.

7500 cells were dispensed in each well in a volume of 160 μl and incubated at 37° C. for 24 h.

Day 2: Test compounds were prepared directly into the media. Nine point concentrations were prepared from 1000 μg/mL to 1.95 μg/mL in two-fold dilutions in fresh medium. The microtiter plates were removed from the incubator and the media replaced with 100 μl of the dilutions of the compound solution. Every set of concentration was done in triplicate, and positive and negative controls were added to each plate. The plates were then incubated for 24 h at 37° C. with 5% $CO_2$ in a humidified atmosphere.

Day 3: The reagent containing the resazurin (CellTiter-Blue, Promega) was diluted in PBS (1:4) and added at 20% (v/v) to each well. The plates were then incubated at 37° C. for 2 h before the fluorescent reduction product was detected.

Media only background values were subtracted before the data was analysed using GraphPad Prism. Compound concentration values were plotted as log values to enable a dose-response curve to be fitted and $IC_{50}$ values determined (Table 7).

TABLE 7

$IC_{50}$ Data for Polymyxin B and Examples 2-14

| Example No | $IC_{50}$ HK-2 cells (μg/mL)[a] |
|---|---|
| Polymyxin B | 11[b] |
| 2 | 87 |
| 3 | 166 |
| 4 | 82 |
| 5 | 250 |
| 6 | 154 |
| 7 | 138 |
| 8 | 497 |
| 9 | 104 |
| 10 | 127 |
| 11 | 310 |
| 12 | >500 |
| 13 | 158 |
| 14 | 60 |

[a]Mean values of up to 6 independent studies;
[b]Mean value of 16 independent studies.

Additional Studies on the In vitro Renal Cell Toxicity Assay

The renal cell toxicity of the additional example compounds was assessed in an in vitro assay using the HK-2 cell as described in the example above. The $IC_{50}$ values for these compounds are set out in Table 7A below. For comparison, the renal cell toxicity Colistin, and CB182,804 (compound 5 in WO2010/075416) and NAB739 were also assessed.

TABLE 7A $IC_{50}$ Data for Colistin and Examples 15-35

| Example No | $IC_{50}$ HK-2 cells (μg/mL)[a] |
|---|---|
| Colistin | 28[a] |
| CB182,804 | 22 |
| NAB739 TFA salt | 176 |
| 15 | 133 |
| 16 | 1000[c] |
| 17 | 84 |
| 18 | >500 |
| 19 | 157[c] |
| 22 | 500[c] |
| 23 | 173 |
| 24 | 101 |
| 25 | 277 |
| 26 | 128 |
| 27 | 118 |
| 28 | 108 |
| 29 | 82 |

TABLE 7A-continued $IC_{50}$ Data for Colistin and Examples 15-35

| Example No | $IC_{50}$ HK-2 cells (μg/mL)[a] |
|---|---|
| 30 | 133 |
| 31 | 93 |
| 32 | 500 |
| 33 | 1000[c] |
| 34 | 86 |
| 35 | 82 |

[a]Mean values of up to 6 independent studies;
[c]solubility issues noted at top concentration Additional Studies on In vivo Nephrotoxicity A model of nephrotoxicity of polymyxins (adapted from Yousef et al., Antimicrob. Agents Chemother., 2011, 55 (9): 4044-4049) was established in rats. The compounds of examples 2, 6, and 14 were examined in the model and compared to Colistin (in its sulphate form). After one week acclimatisation, male Sprague-Dawley rats were surgically prepared with a jugular cannula and were housed individually, as required, either in pre-assigned housing cages or metabolic cages. Colistin and the example compounds were prepared in saline. Compounds were introduced via the jugular canula twice a day 7 hours apart for seven days. Each dose was increased progressively for three days up to the top dose that was then administered until termination of the study. Twenty-four hour urine collection (on ice) was performed at pre-dose and on days 4 and 7. The dose regimen is set out in Table 8 below.

TABLE 8

Dose regimen used in the in vivo nephrotoxicity study. Doses are indicated in mg drug base/kg.

| Dose regimens | Day 1 | | Day 2 | | Day 3 | | Day 4 to Day 7 or Day 10 | |
|---|---|---|---|---|---|---|---|---|
| | a.m. | p.m. | a.m. | p.m. | a.m. | p.m. | a.m. | p.m. |
| 2 mg/kg bid | 0.25 | 0.5 | 0.625 | 0.625 | 0.875 | 1.375 | 2 | 2 |
| 8 mg/kg bid | 1 | 2 | 2.5 | 2.5 | 3.5 | 5.5 | 8 | 8 |

The activity in urine of the N-acetyl-beta-D-glucosaminidase (NAG) was determined spectrophotometrically using the NAG assay kit from Roche Applied Science. Biomarkers of kidney injury were determined using the Kidney Injury Panel II from the Multi-Spot® Assay System (Meso Scale Discovery).

Figure 2:
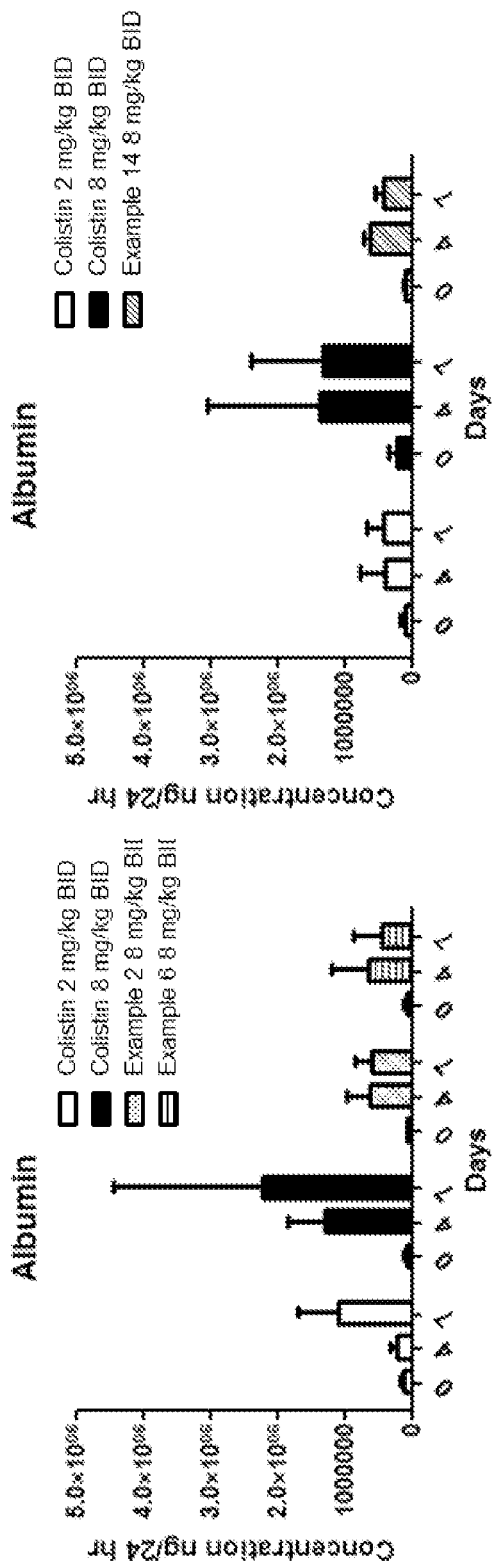
Figure 3:
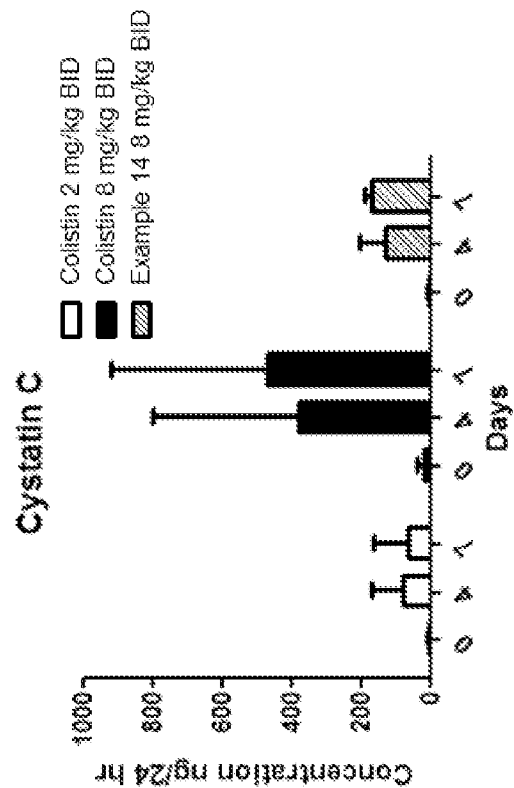
Figure 3:
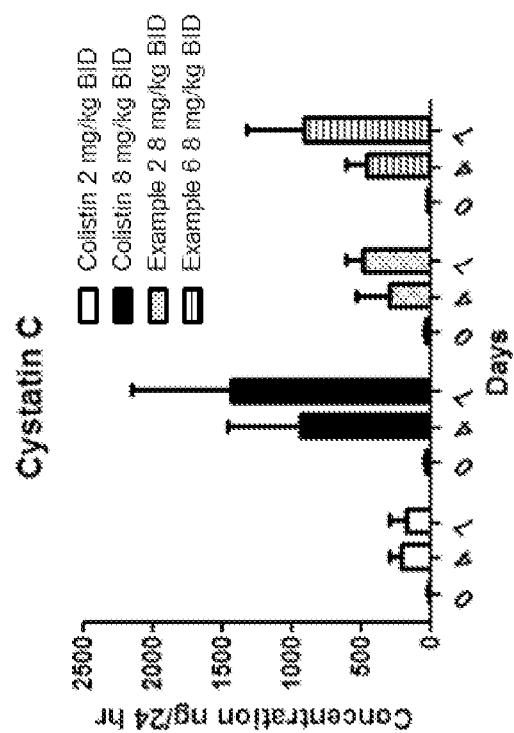

Examples 2, 6, and 14 dosed using the 8 mg/kg regimen showed significantly reduced levels of the renal biomarkers NAG, albumin and cystatin C compared to Colistin at the same dose regimen (see FIGS. 1 to 3). The response was similar to that elicited by Colistin at a maximum concentration of 2 mg/kg.

FIG. 1 shows the concentration of NAG (ng/24 h) at days 0, 4 and 7 for compounds 2, 6, and 14 and Colistin. The left-hand graph shows from left to right Colistin (2 mg/kg BID), Colistin (8 mg/kg BID), compound 2 (8 mg/kg BID) and 6 (8 mg/kg BID). The right-hand graph shows Colistin (2 mg/kg BID), Colistin (8 mg/kg BID) and compound 14 (8 mg/kg BID).

FIG. 2 shows the concentration of albumin (ng/24 h) at days 0, 4 and 7 for compounds 2, 6, and 14 and Colistin. The left-hand graph shows from left to right Colistin (2 mg/kg BID), Colistin (8 mg/kg BID), compound 2 (8 mg/kg BID)

and 6 (8 mg/kg BID). The right-hand graph shows Colistin (2 mg/kg BID), Colistin (8 mg/kg BID) and compound 14 (8 mg/kg BID).

FIG. 3 shows the concentration of cystatin C (ng/24 h) at days 0, 4 and 7 for compounds 2, 6, and 14 and Colistin. The left-hand graph shows from left to right Colistin (2 mg/kg BID), Colistin (8 mg/kg BID), compound 2 (8 mg/kg BID) and 6 (8 mg/kg BID). The right-hand graph shows Colistin (2 mg/kg BID), Colistin (8 mg/kg BID) and compound 14 (8 mg/kg BID).

The invention claimed is:
1. A compound of the formula (I):

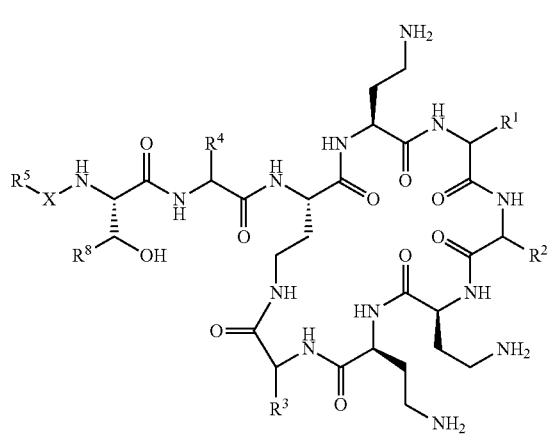

wherein:
X represents an —C(O)—, —NHC(O)—, —OC(O)—, —CH$_2$— or —SO$_2$—; and
R$^1$ together with the carbonyl group and nitrogen alpha to the carbon to which it is attached, represents a phenylalanine, leucine or valine residue;
R$^2$ together with the carbonyl group and nitrogen alpha to the carbon to which it is attached, represents a leucine, iso-leucine, phenylalanine, threonine, valine or nor-valine residue;
R$^3$ together with the carbonyl group and nitrogen alpha to the carbon to which it is attached, represents a threonine or leucine residue;
R$^4$ together with the carbonyl group and nitrogen alpha to the carbon to which it is attached, represents an α,γ-diaminobutyric acid or serine residue;
R$^5$ represents a group (a) to (g), where:
(a) is C$_{0-12}$ alkyl(C$_{3-8}$ cycloalkyl) and C$_{0-12}$ alkyl is selected from the group consisting of methyl, ethyl, n-propyl, iso-propyl, butyl, n-butyl and tert-butyl, wherein the alkyl or the cycloalkyl is substituted with (i) one, two or three hydroxyl groups, or (ii) one —NR$^6$R$^7$ group, or (iii) one —NR$^6$R$^7$ group and one or two hydroxyl groups;
(b) is C$_{2-12}$ alkyl, wherein the alkyl is substituted with (i) one, two or three hydroxyl groups, or (ii) one —NR$^6$R$^7$ group at a terminal of the alkyl chain, or (iii) one —NR$^6$R$^7$ group and two hydroxyl groups;
(c) is C$_{0-12}$ alkyl(C$_{4-6}$ heterocyclyl);
(d) is C$_{3-8}$ cycloalkyl, and the cycloalkyl is substituted with (i) one, two or three hydroxyl groups, or (ii) one —N$^6$R$^7$ group and one or two hydroxyl groups;
(e) is C$_{3-12}$ alkyl, such as C$_{3-10}$ alkyl, wherein the alkyl is substituted with one —NR$^6$R$^7$ group and one hydroxyl group;
(f) is C$_{6-12}$ alkyl substituted with one —NR$^6$R$^7$ group; and
(g) is C$_5$ cyloalkyl substituted with one —NR$^6$R$^7$ group;
R$^6$ represents hydrogen or C$_{1-4}$ alkyl; and
R$^7$ represents hydrogen or C$_{1-4}$ alkyl,
R$^8$ represents methyl or hydrogen, or
a prodrug thereof, and/or
a pharmaceutically acceptable salt thereof.

2. A compound of formula (I) according to claim 1 where R$^1$ together with the carbonyl group and nitrogen alpha to the carbon to which it is attached represents a phenylalanine residue.

3. A compound of formula (I) according to claim 2 where the phenylalanine is D-phenylalanine.

4. A compound of formula (I) according to claim 1 where R$^2$ together with the carbonyl group and nitrogen alpha to the carbon to which it is attached represents a leucine residue.

5. A compound of formula (I) according to claim 1 where R$^3$ together with the carbonyl group and nitrogen alpha to the carbon to which it is attached represents a threonine residue.

6. A compound of formula (I) according to claim 1 where R$^4$ together with the carbonyl group and nitrogen alpha to the carbon to which it is attached represents an α,γ-diaminobutyric acid residue.

7. A compound of formula (I) according to claim 1 wherein R$^6$ is hydrogen or methyl.

8. A compound of formula (I) according to claim 1 wherein R$^7$ is hydrogen or methyl.

9. A compound of formula (I) according to claim 1 where X is —C(O)—.

10. A compound according to claim 1 selected from the group consisting of:
2-Hydroxyoctanoyl polymyxin B nonapeptide;
3-Aminopropanoyl polymyxin B nonapeptide;
3-(N,N-Dimethylamino)-propanoyl polymyxin B nonapeptide;
4-Aminobutanoyl polymyxin B nonapeptide;
6-Aminohexanoyl polymyxin B nonapeptide;
8-Hydroxyoctanoyl polymyxin B nonapeptide;
8-Aminooctanoyl polymyxin B nonapeptide;
3-(N-Methylamino)propanoyl polymyxin B nonapeptide;
2-Amino cyclopentane carbonyl polymyxin B nonapeptide;
3-Aminopropanoyl colistin (polymyxin E) nonapeptide;
3-Pyrrolidine-3-carbonyl polymyxin B nonapeptide;
3-Amino-3-cyclohexanepropanoyl polymyxinB nonapeptide;
5-Aminopentanoyl polymyxin B nonapeptide;
3-Hydroxyoctanoyl polymyxin B nonapeptide;
4-(N,N-dimethylamino)-butanoyl polymyxin B nonapeptide;
7-Aminoheptanoyl polymyxin B nonapeptide;
4-Morpholinylbutanoyl polymyxin B nonapeptide;
6-Hydroxyhexanoyl polymyxin B nonapeptide;
3-Hydroxybutanoyl polymyxin B nonapeptide;
4-(N-methylamino)-butanoyl polymyxin B nonapeptide;
4-Aminobutanoyl polymyxin E nonapeptide;
2-Hydroxyoctanoyl polymyxin E nonapeptide;
4-Amino-5-methylhexanoyl polymyxin B nonapeptide;
3-(1-Pyrrolidin-2-yl)-propionyl polymyxin B nonapeptide;
trans-4-Hydroxycyclohexanecarbonyl polymyxin B nonapeptide;
3-Hydroxypropanoyl polymyxin B nonapeptide;

(2-Hydroxy-2-cyclohexyl)ethanoyl polymyxin B nonapeptide;

2-Amino octanoyl polymyxin B nonapeptide; and a pharmaceutically acceptable salt thereof.

11. A pharmaceutical composition comprising a compound of formula (I) or a pharmaceutically acceptable salt thereof as defined in claim 1 together with a pharmaceutically acceptable carrier.

12. A compound according to claim 1 wherein $R^5$ is $C_{0-12}$ alkyl($C_{3-8}$ cycloalkyl) and $C_{0-12}$ alkyl is selected from the group consisting of methyl, ethyl, n-propyl, iso-propyl, butyl, n-butyl and tert-butyl, wherein the alkyl or the cycloalkyl is substituted with (i) one, two or three hydroxyl groups, or (ii) one —$NR^6R^7$ group, or (iii) one —$NR^6R^7$ group and one or two hydroxyl groups.

13. A compound according to claim 1 wherein $R^5$ is $C_{0-12}$ alkyl($C_{3-8}$ cycloalkyl) wherein the alkyl or the cycloalkyl is substituted with one —$NR^6R^7$ group.

14. A compound according to claim 1 wherein the $C_{3-8}$ cycloalkyl is $C_5$ or $C_6$ cycloalkyl.

15. A compound according to claim 1 wherein $R^5$ is $C_{2-12}$ alkyl wherein the alkyl is substituted with (i) one, two or three hydroxyl groups, or (ii) a —$NR^6R^7$ group at a terminal of the alkyl chain, or (iii) one —$NR^6R^7$ group and two hydroxyl groups.

16. A compound according to claim 15, wherein $R^5$ is $C_{2-12}$ alkyl is substituted with a —$NR^6R^7$ group at a terminal of the alkyl chain.

17. A compound according to claim 15 wherein $R^5$ is $C_{2-12}$ alkyl is substituted with one, two or three hydroxyl groups.

18. A compound according to claim 1, wherein $R^5$ is $C_{0-12}$ alkyl($C_{4-6}$ heterocyclyl).

19. A compound according to claim 1, wherein $R^5$ is $C_{3-8}$ cycloalkyl, and the cycloalkyl is substituted with (i) one, two or three hydroxyl groups, or (ii) one —$NR^6R^7$ group and one or two hydroxyl groups.

20. A compound according to claim 1 wherein $R^5$ is $C_{3-12}$ alkyl, wherein the alkyl is substituted with one —$NR^6R^7$ group and one hydroxyl group.

21. A compound according to claim 1, wherein $R^5$ is $C_{6-12}$ alkyl substituted with one —$NR^6R^7$ group.

22. A compound according to claim 1, wherein $R^5$ is $C_5$ cycloalkyl substituted with one —$NR^6R^7$ group.

23. A compound of formula (I) according to claim 1 wherein $R^8$ is methyl.

24. A method of treating a bacterial infection comprising administering to a subject in need thereof a therapeutically effect amount of a compound according to claim 1.

25. A method according to claim 24 where the bacterium is multidrug resistant.

26. A method according to claim 24 where the bacterium is Gram negative.

* * * * *